(12) United States Patent
Borrebaeck et al.

(10) Patent No.: US 10,564,163 B2
(45) Date of Patent: Feb. 18, 2020

(54) METHOD, ARRAY AND USE THEREOF

(71) Applicant: IMMUNOVIA AB, Lund (SE)

(72) Inventors: Carl Arne Krister Borrebaeck, Lund (SE); Christer Lars Bertil Wingren, Sodra Sandby (SE)

(73) Assignee: IMMUNOVIA AB, Lund (SE)

( * ) Notice: Subject to any disclaimer, the term of this patent is extended or adjusted under 35 U.S.C. 154(b) by 0 days.

(21) Appl. No.: 15/874,154

(22) Filed: Jan. 18, 2018

(65) Prior Publication Data

US 2018/0313852 A1 Nov. 1, 2018

Related U.S. Application Data

(63) Continuation of application No. 13/702,756, filed as application No. PCT/GB2011/000865 on Jun. 9, 2011, now abandoned.

(30) Foreign Application Priority Data

Jun. 11, 2010 (GB) .................................. 1009798.8

(51) Int. Cl.
*G01N 33/68* (2006.01)
*G01N 33/543* (2006.01)
*G01N 33/574* (2006.01)

(52) U.S. Cl.
CPC . *G01N 33/57415* (2013.01); *G01N 33/54366* (2013.01); *G01N 33/6893* (2013.01)

(58) Field of Classification Search
CPC ......... G01N 33/6893; G01N 33/57415; G01N 33/54366
See application file for complete search history.

(56) References Cited

U.S. PATENT DOCUMENTS 4,376,110 A 3/1983 David et al.
4,486,530 A 12/1984 David et al.
(Continued)

FOREIGN PATENT DOCUMENTS

JP 2010151800 A 7/2010
WO 99/49083 A1 9/1990
(Continued)

OTHER PUBLICATIONS

Wingren and Borreback (Cur. Op. Biotech., 2008, 19:55-61) (Year: 2008).*

(Continued)

*Primary Examiner* — Jeremy C Flinders
(74) *Attorney, Agent, or Firm* — Robert C. Netter, Jr.; Dann, Dorfman, Herrell & Skillman

(57) ABSTRACT

The present invention provides methods and arrays for the prognosis and treatment of breast cancer in a subject. In a particular embodiment, the methods comprise the steps of: (a) providing a first proteome sample from the subject; (b) measuring in the first proteome sample the amount of two or more biomarkers selected from the group of biomarkers listed in Table 1; (c) providing an additional proteome sample from the subject; (d) measuring in the additional proteome sample the amount of the two or more biomarkers selected from the group of biomarkers listed in Table 1 measured in step (b); (e) determining the difference between the amount of the one or more biomarkers in the first and additional proteome samples; (f) calculating biomarker velocities; (g) determining a risk of recurrence of breast cancer; and (h) treating the subject.

18 Claims, 7 Drawing Sheets

(56) References Cited

U.S. PATENT DOCUMENTS

Figure 1A:
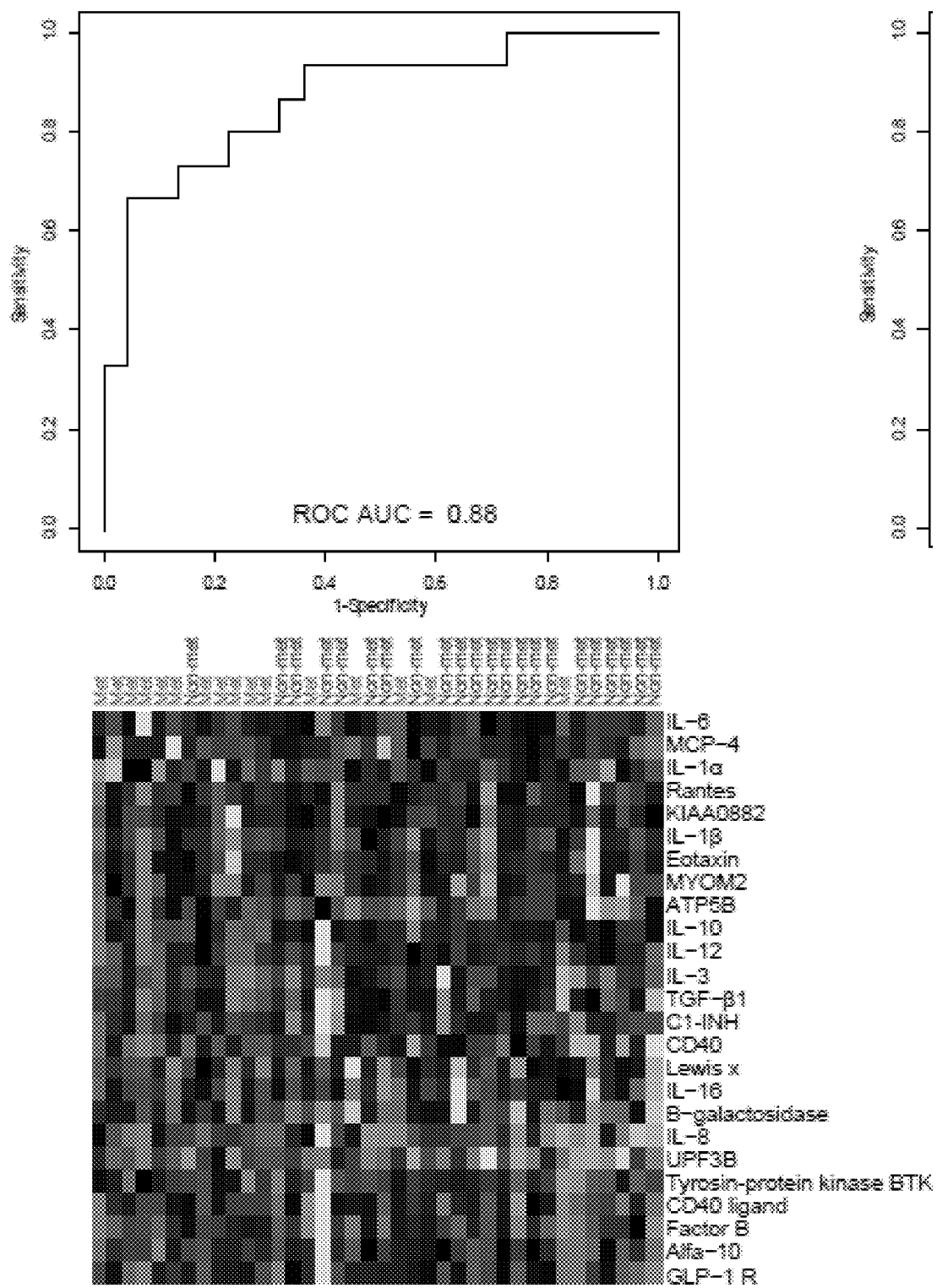

| | | |
|---|---|---|
| 5,376,531 A | 12/1994 | Anderson et al. |
| 5,856,090 A | 1/1999 | Epstein |
| 6,326,161 B1 | 12/2001 | Puscas et al. |
| 2003/0120057 A1 | 6/2003 | Reddy et al. |
| 2004/0087571 A1 | 5/2004 | Brown et al. |
| 2004/0259161 A1 | 12/2004 | Nilsson et al. |
| 2006/0094056 A1 | 5/2006 | Chappell et al. |
| 2008/0026950 A1 | 1/2008 | Emi et al. |
| 2009/0166224 A1 | 7/2009 | Yang et al. |
| 2011/0086349 A1 | 4/2011 | Anjomshoaa et al. |

FOREIGN PATENT DOCUMENTS

| | | |
|---|---|---|
| WO | 1997/025426 A3 | 7/1997 |
| WO | 1998/037186 A1 | 8/1998 |
| WO | 1998/041649 A2 | 9/1998 |
| WO | 2000/009561 A1 | 2/2000 |
| WO | 2002/101357 A2 | 12/2002 |
| WO | 2004/037996 A2 | 5/2004 |
| WO | 2004/106495 A2 | 12/2004 |
| WO | 2005/005601 A2 | 1/2005 |
| WO | 2005/040806 A2 | 5/2005 |
| WO | 2006/105642 A1 | 10/2006 |
| WO | 2007/002069 A2 | 1/2007 |
| WO | 2007/022248 A2 | 2/2007 |
| WO | 2007/045996 A1 | 4/2007 |
| WO | 2007/056011 A2 | 5/2007 |
| WO | 2007/068985 A2 | 6/2007 |
| WO | 2009/114862 A1 | 6/2007 |
| WO | 2008/048193 A2 | 4/2008 |
| WO | 2008/117067 A2 | 10/2008 |
| WO | 2009/068857 A1 | 6/2009 |
| WO | 2009/118205 A2 | 10/2009 |
| WO | 2009/132909 A1 | 11/2009 |
| WO | 2010/076322 A1 | 7/2010 |
| WO | 2010/088386 A1 | 8/2010 |
| WO | 2011/063274 A2 | 5/2011 |
| WO | 2011/154698 A2 | 12/2011 |
| WO | 2015/189591 A2 | 12/2015 |

OTHER PUBLICATIONS

Carrlson et al. (Eur. J. Cancer, 2008, 44:472-480) (Year: 2008).*

Al-Rawi, M.A.A., et al., "Aberrant Expression of Interleukin-7 (IL-7) and its Signalling Complex in Human Breast Cancer," Eur. J. Cancer (2004) 40:494-502.

Anders, C., et al., "1002—Antibody Microarray Based Oncoproteomics—Analysis of Breast Cancer Proteomes," Breast Cancer Res. Treat. (2006) 100(Suppl 1):S39.

Borrebaeck, C.A.K., et al., "Antibody Microarray-based Oncoproteomics," Expert Opin. Biol. Ther. (2006) 6 (8):833-838.

Neckelmann, N., et al., "The Human ATP Synthase β Subunit Gene: Sequence Analysis, Chromosome Assignment, and Differential Expression," Genomics (1989) 5(4):829-843.

Wenke, A.K., et al., "Expression of Integrin Alpha10 is Induced in Malignant Melanoma," Cellular Oncology (2007) 29:373-386.

Chavey, C., et al., "Oestrogen Receptor Negative Breast Cancers Exhibit High Cytokine Content," Breast Cancer Res. (2007) 9(1):R15.

Chen, G., et al., "Discordant Protein and mRNA Expression in Lung Adenocarcinomas," Molecular & Cellular Proteomics (2002) 1(4):304-313.

Pepe, M.S., et al. "Phases of Biomarker Development for Early Detection of Cancer," J. Natl. Cancer Inst. (2001) 93 (14):1054-1061.

Custodio, A.B., et al., "PP38—Proteomic Analysis of Plasma from BRCA/BRCA2 Mutation Carriers as Modifier Risk Factor of Breast Cancer," EJC Supplements (2009) 7(4):15.

Dehqanzada, Z.A., et al., "Assessing Serum Cytokine Profiles in Breast Cancer Patients Receiving a HER2/neu Vaccine using Luminex® Technology," Oncology Reports (2007) 17:687-694.

De Sousa Abreu, R., et al., "Global Signatures of Protein and mRNA Expression Levels," Mol. Biosyst. (2009) 5 (12)1512-1526.

Donnelly, T.J., et al., "Cytokine, Complement, and Endotoxin Profiles Associated with the Development of the Adult Respiratory Distress Syndrome After Severe Injury," Crit. Care Med. (1994) 22(5):768-76.

Drukier, A.K., "High-Sensitivity Blood-Based Detection of Breast Cancer by Multi Photon Detection Diagnostic Proteomics," J. Proteome Res. (2006) 5:1906-1915.

Goncalves, A., et al., "Postoperative Serum Proteomic Profiles may Predict Metastatic Relapse in High-risk Primary Breast Cancer Patients Receiving Adjuvant Chemotherapy," Oncogene (2006) 25:981-989.

Gry, M., et al., "Correlations between RNA and Protein Expression Profiles in 23 Human Cell Lines," BMC Genomics (2009) 10:365.

Obradovic, Z., et al., "Mining of Microarray, Proteomics, and Clinical Data for Improved Identification of Chronic Fatigue Syndrome" Critical Assessment of Microarray Data Analysis (CAMDA), Jun. 8, 2006 (available at http://camda.duke.edu/camda06/papers/index.html).

Ho, C.L., et al., "Global Cytokine Analysis in Myeloproliferative Disorders," Leukemia Res. (2007) 31:1389-1392.

Holzel, D., et al., "True Local Recurrences do not Metastasize," Cancer Metastasis Rev. (2011) 30:161-176.

Vazquez-Martin, A., et al., "Protein Array Technology to Detect HER2 (erbB-2)-induced 'Cytokine Signature' in Breast Cancer," Eur. J. Cancer (2007) 43:1117-1124.

Slobodova, Z., et al., "P1.33—Analysis of Immunohistochemical Expression of CD40 in Breast Cancer and its Relation to Prognosis," Virchows Arch. (2009) 455 (Suppl 1):S104.

Speirs, V., et al., "Interleukin-3: A Putative Protective Factor Against Breast Cancer Which is Secreted by Male But Not Female Breast Fibroblasts," Int. J. Cancer (1995) 61:416-419.

Kurebayashi, J., et al., "Combined Measurement of Serum Sialyl Lewis X with Serum CA15-3 in Breast Cancer Patients," Jpn. J. Clin. Oncol. (2006) 36(3):150-153.

Lamoureux, G., et al., "Biologic Markers and Breast Cancer: A Multiparametric Study-1. Increased Serum Protein Levels," Cancer (1982) 49(3):502-512.

Lane, D.M., et al., "Serum Lipids and Apolipoproteins in Women with Breast Masses," Breast Cancer Res. Treat. (1995) 34(2):161-169.

Lee, K.M., et al., "Genetic Polymorphisms of TGF-B1 & TNF-B and Breast Cancer Risk," Breast Cancer Res. Treat. (2005) 90(2):149-155.

Li, J., et al., "Independent Validation of Candidate Breast Cancer Serum Biomarkers Identified by Mass Spectrometry," Clinical Chem. (2005) 51(12):2229-2235.

Zutter, M.M., et al., "Altered Integrin Expression in Adenocarcinoma of the Breast," Amer. J. Pathol. (1993) 142(5): 1439-1448.

Makarov, D.V., et al., "Biomarkers for Prostate Cancer," Annu. Rev. Med. (2009) 60:139-51.

Mackay, A., et al. "Molecular response to aromatase inhibitor treatment in primary breast cancer." Breast Cancer Res. 2007;9(3):R37.

Harvell, D.M., et al. "Molecular signatures of neoadjuvant endocrine therapy for breast cancer: characteristics of response or intrinsic resistance." Breast Cancer Res Treat 2008 Dec;112(3):475-88.

Carlsson, A., et al. "Molecular serum portraits in patients with primary breast cancer predict the development of distant metastases." Proc Natl Acad Sci U S A. Aug. 23, 2011;108(34):14252-7.

Carlsson, A., et al. "Serum proteome profiling of metastatic breast cancer using recombinant antibody microarrays." Eur J Cancer. Feb. 2008;44(3):472-80.

Huang, T.C., et al. "Targeting therapy for breast carcinoma by ATP synthase inhibitor aurovertin B." J Proteome Res. Apr. 2008;7(4):1433-44.

Villanueva, J., et al. "Differential exoprotease activities confer tumor-specific serum peptidome patterns." J Clin Invest. Jan. 2006;116(1):271-84.

Isidoro, A., et al. "Breast carcinomas fulfill the Warburg hypothesis and provide metabolic markers of cancer prognosis." Carcinogenesis. Dec. 2005;26(12):2095-104.

(56) References Cited

OTHER PUBLICATIONS

Cuezva, J.M., et al. "The tumor suppressor function of mitochondria: translation into the clinics." Biochim Biophys Acta. Dec. 2009;1792(12):1145-58.
Isidoro, A., et al. "Alteration of the bioenergetic phenotype of mitochondria is a hallmark of breast, gastric, lung and oesophageal cancer." Biochem J. Feb. 15, 2004;378(Pt 1):17-20.
Wang, Y., et al., "Gene-expression profiles to predict distant metastasis of lymph-node-negative primary breast cancer" Lancet 2005 365(9460):671-9.
Lin, et al., "Identification of interleukin-8 as estrogen receptor-regulated factor involved in breast cancer invasion and angiogenesis by protein arrays" Int. J. Cancer (2004) 109(4):507-15.
Lin, et al., "Profiling of cytokine expression by biotin-labeled-based protein arrays" Proteomics (2003) 3(9):1750-7.
Lin, et al., "[Effect of interleukin-8 in cell invasion and proliferation of human breast cancer]" Zhonghua Wai Ke Za Zhi (2005)43(23):1541-4 [Abstract Only].
Smith, et al., "The analysis of doxorubicin resistance in human breast cancer cells using antibody microarrays" Mol. Cancer Ther. (2006) 5(8):2115-20.
Hudelist, et al., "Use of high-throughput protein array for profiling of differentially expressed proteins in normal and malignant breast tissue" Breast Cancer Res. Treat. (2004) 86(3):281-91.
Eisen, et al., "Cluster analysis and display of genome-wide expression patterns" Proc. Natl. Acad. Sci. (1998) 95 (25):14863-8.
Ingvarsson, et al., "One-step fractionation of complex proteomes enables detection of low abundant analytes using antibody-based microarrays" J. Proteome Res. (2006) 5(1):170-6.
Bartling, et al., "Comparative application of antibody and gene array for expression profiling in human squamous cell lung carcinoma" Lung Cancer (2005) 49(2):145-54.
Zhou, et al., "Two-color, rolling-circle amplification on antibody microarrays for sensitive, multiplexed serum-protein measurements" Genome Biol. (2004) 5(4):R28.
Mor, et al., "Serum protein markers for early detection of ovarian cancer" Proc. Natl. Acad. Sci. (2005) 102 (21):7677-82.
Wingren, et al., "High-throughput proteomics using antibody microarrays" Expert Rev. Proteomics (2004) 1 (3)355-64.
Gao, et al., "Distinctive serum protein profiles involving abundant proteins in lung cancer patients based upon antibody microarray analysis" BMC Cancer (2005) 5:110.
Sahu, et al., "Structure and biology of complement protein C3, a connecting link between innate and acquired Immunity" Immunol. Rev. (2001) 180:35-48.
Ben-Baruch, A. "Host microenvironment in breast cancer development: inflammatory cells, cytokines and chemokines in breast cancer progression: reciprocal tumor-microenvironment interactions" Breast Cancer Res. (2003) 5(1):31-36.
Simson, et al., "Regulation of carcinogenesis by IL-5 and CCL11: a potential role for eosinophils in tumor immune surveillance" J. Immunol. (2007) 178(7):4222-9.
Vudatta, et al. "Reduced numbers of IL-7 receptor (CD127) expressing immune cells and IL-7-signaling defects in peripheral blood from patients with breast cancer" Int. J. Cancer (2007) 121:1512-1519.
Menten, et al., "Monocyte chemotactic protein-3" Eur. Cytokine Netw. (2001) 12(4):554-60.
Al-Rawi, et al., "Interleukin 7 induces the growth of breast cancer cells through a wortmannin-sensitive pathway" Br. J. Surg. (2004) 91(1):61-8.
Vitolo, et al., "Interleukin-12-related cytokine gene expression in carcinomas of the breast, lung, and larynx: a study at tissue level" Cancer Detect Prev. (2000) 24(5):422-34.
Ellsworth, et al., "A gene expression signature that defines breast cancer metastases" Clin. Exp. Metastasis (2009) 26:205-213.
Troup, et al., "Reduced expression of the small leucine-rich proteoglycans, lumican and decorin is associated with poor outcome in node-negative invasive breast cancer" Clin. Cancer Res. (2003) 9:207-214.

Chakravati, S., "Focus on molecules: Keratocan (KERA)" Experimental Eye Research (2006) 82:183-184.
Pitteri, et al. "Detection of elevated plasma levels of epidermal growth factor receptor before breast cancer diagnosis among hormone therapy users" Cancer Research (2010) 70(21): 8598-8606.
Li, C.I., "Discovery and validation of breast cancer early detection biomarkers in preclinical samples" Hormones and Cancer (2011) 2(2):125-131.
Ho, et al., "Global cytokine analysis in myeloproliferative disorders" Leukaemia Research (2007) 31:1389-1392.
Gu, et al., "The expression of CD15mRNA, CD44vmRNA and nm23H1mRNA in breast cancer tissue and its clinical significance" Chinese Medical Journal (2000) 80(11): 854-857 [Abstract Only].
Enard, et al., "Intra- and interspecific variation in primate gene expression patterns" Science (2002) 296:340-3.
Cobb, et al., "Sepsis gene expression profiling: Murine splenic compared with hepatic responses determined by using complementary DNA microarrays" Crit. Care Med. (2002) 30:2711.
Cheung, et al., "Natural variation in human gene expression assessed in lymphoblastoid cells" Nature Genetics (2003) 33:422.
Wu, T.D., "Analysing gene expression data from DNA microarrays to identify candidate genes" Journal of Pathology (2001) 195:53.
Newton, et al. "On differential variability of expression ratios: improving statistical inference about gene expression changes from microarray data" Journal of Computational Biology (2001) 8:37.
Pang, et al., "Analysing breast cancer microarrays from African Americans using shrinkage-based discriminant analysis" Human Genomics (2010) 5(1):5-16.
Ausubel et al., Short Protocols in Molecular Biology (4th edition) Wiley, New York), Section 10.5.
National Center for Biotechnology Information, Medical Subject Heading "Interleukin-6" (1990) obtained at: https://www.ncbi.nlm.nih.gov/mesh/68015850.
National Center for Biotechnology Information, Medical Subject Heading "Interleukin-7" (1990) obtained at: https://www.ncbi.nlm.nih.gov/mesh/68015851.
Soderlind, et al., "Recombining germline-derived CDR sequences for creating diverse single-framework antibody libraries" Nat Biotechnol (2000) 18:852-856.
Ingvarsson, et al., "Design of recombinant antibody microarrays for serum protein profiling: targeting of complement proteins" J. Proteome Res. (2007) 6:3527-36.
Hamelinck, et al. "Optimized normalization for antibody microarrays and application to serum-protein profiling" Mol cell Proteomics (2005) 4:773-84.
Schervish, M.J. "A Review of Multivariate Analysis" Statistical Science (1987) 2(4):396-413.
Anonymous, National Institute for Health and Care Excellence (NICE), Clinical Guideline 80 "Early and locally advanced breast cancer: Diagnosis and treatment" (2009) (obtained at http://www.nice.org.uk/nicemedia/pdf/CG80NICEGuideline.pdf).
Benjamini, et al., "Controlling the false discovery rate: a practical and powerful approach to multiple testing" J. Royal Stat. Soc. Series B (1995) 57:289-300.
Bergamaschi, et al., "Extracellular matrix signature identifies breast cancer subgroups with different clinical outcome" J Pathology (2008) 214:357-367.
Bierie, et al. "Tumour microenvironment: TGFbeta: the molecular Jekyll and Hyde of cancer" Nature Reviews Cancer (2006) 6:506-520.
Borrebaeck, et al. (2011) "Recombinant antibodies for the generation of antibody arrays" Methods Mol Biol (2011) 785:247-262.
Bouchal, et al., "Biomarker discovery in low-grade breast cancer using isobaric stable isotope tags and two-dimensional liquid chromatography-tandem mass spectrometry (iTRAQ-2DLC-MS/MS) based quantitative proteomic analysis" J Proteome Research (2009) 8:362-373.
Ciocca, et al., "Molecular markers for predicting response to tamoxifen in breast cancer patients" Endocrine (2000) 13:1-10.
Cortes, et al., "Support-Vector Networks" Machine Learning (1995) 20:273-297.

(56) References Cited

OTHER PUBLICATIONS

Cortez, et al., "Minichromosome maintenance proteins are direct targets of the ATM and ATR checkpoint kinases" Proceedings of the National Academy of Sciences of the United States of America (2004) 101:10078-10083.

Desmedt, et al., "Biological processes associated with breast cancer clinical outcome depend on the molecular subtypes" Clinical Cancer Research (2008) 14:5158-5165.

Deutsch, et al., "PeptideAtlas: a resource for target selection for emerging targeted proteomics workflows" EMBO Reports (2008) 9:429-434.

Dowsett, et al., "International Web-based consultation on priorities for translational breast cancer research" Breast cancer Research (2007) 9:R81.

Elston, et al., "Pathological prognostic factors in breast cancer. I. The value of histological grade in breast cancer: experience from a large study with long-term follow-up" Histopathology (1991) 19:403-410.

Fata, et al., "Regulation of mammary gland branching morphogenesis by the extracellular matrix and its remodeling enzymes" Breast cancer research (2004) 6:1-11.

Frierson, et al. "Interobserver reproducibility of the Nottingham modification of the Bloom and Richardson histologic grading scheme for infiltrating ductal carcinoma" (1995) American Journal of Clinical Pathology (1995) 103:195-198.

Geiger, et al., "Super-SILAC mix for quantitative proteomics of human tumor tissue" Nature Methods (2010) 7:383-385.

Gong, et al., "Proteome profile of human breast cancer tissue generated by LC-ESI-MS/MS combined with sequential protein precipitation and solubilization" J Proteome Research (2008) 7:3583-3590.

Ha, et al. "Cancer-associated expression of minichromosome maintenance 3 gene in several human cancers and its Involvement in tumorigenesis" Clinical Cancer Research (2004) 10:8386-8395.

Hakkinen, et al., "The proteios software environment: an extensible multiuser platform for management and analysis of proteomics data" J Proteome Research (2009) 8:3037-3043.

Hanahan, et al., "The hallmarks of cancer" Cell (2000) 100:57-70.

Hanahan, et al. "Hallmarks of cancer: the next generation" Cell (2011) 144:646-674.

Hanash, S. "Disease proteomics" Nature (2003) 422:226-232.

Hinatyszyn, et al. "Correlation of GREB1 mRNA with protein expression in breast cancer: validation of a novel GREB1 monoclonal antibody" Breast Cancer Research and Treatment (2010) 122:371-380.

Hondermarck, et al., "Proteomics of breast cancer: the quest for markers and therapeutic targets" J Proteome Research (2008) 7:1403-1411.

Hudis, C.A. "Trastuzumab—mechanism of action and use in clinical practice" New England J Medicine (2007) 357:39-51.

Ivshina, et al., "Genetic reclassification of histologic grade delineates new clinical subtypes of breast cancer" Cancer Research (2006) 66:10292-10301.

Jemal, et al., "Global cancer statistics" CA CAancer J Clin (2011) 61:69-90.

Johnson, et al., "Compromised CDK1 activity sensitizes BRCA-proficient cancers to PARP inhibition" Nature Medicine (2011) 17:875-882.

Kang, et al., "Proteomic molecular portrait of interface zone in breast cancer" J Proteome Research (2010) 9:5638-5645.

Kuhn, et al., "Structure and function of poly(A) binding proteins" Biochimica et biophysica acta (2004) 1678:67-84.

Lasko, et al. "The use of receiver operating characteristic curves in biomedical informatics" J Biomedical Informatics (2005) 38:404-415.

Malumbres, et al., "Cell cycle, CDKs and cancer: a changing paradigm" Nature Reviews Cancer (2009) 9:153-166.

Mangus, et al., "Poly(A)-binding proteins: multifunctional scaffolds for the post-transcriptional control of gene expression" Genome Biology (2003) 4:223.

Mckiernan, et al., "The role of S100 genes in breast cancer progression" Tumour Biology (2011) 32:441-450.

Moon, et al., "Kruppel-like factor 4 (KLF4) activates the transcription of the gene for the platelet isoform of phosphofructokinase (PFKP) in breast cancer" Journal Biological Chemistry (2011) 286:23808-23816.

Nadler, et al., "Growth factor receptor-bound protein-7 (Grb7) as a prognostic marker and therapeutic target in breast cancer" Annals of oncology (2010) 21:466-473.

Olsson, et al., "Proteomic analysis and discovery using affinity proteomics and mass spectrometry" Molecular & Cellular Proteomics (2011) 10:M110 003962.

Pavlidis, et al., "Matrix2png: a utility for visualizing matrix data" Bioinformatics (2003) 19:295-296.

Perou, et al., "Molecular portraits of human breast tumours" Nature (2000) 406:747-752.

Phillips, et al., "Clinical practice patterns and cost effectiveness of human epidermal growth receptor 2 testing strategies in breast cancer patients" Cancer (2009) 115:5166-5174.

Place, et al., "The microenvironment in breast cancer progression: biology and implications for treatment" Breast Cancer Research (2011) 13:227.

Rae, et al., "GREB 1 is a critical regulator of hormone dependent breast cancer growth" Breast Cancer Research and Treatment (2005) 92:141-149.

Ringner, et al., "GOBO: gene expression-based outcome for breast cancer online" PloS one (2011) 6:e17911.

Robbins, et al., "Histological grading of breast carcinomas: a study of interobserver agreement" Human Pathology (1995) 26:873-879.

Rochefort, et al., "How to target estrogen receptor-negative breast cancer?" Endocrine-related cancer (2003) 10:261-266.

Meyer, et al., "e1071: Misc Functions of the Department of Statistics, Probability Theory Group" (2019) obtained at 1. http://cran.r-project.org/web/packages/e1071/index.html.

Slamon, et al., "Use of chemotherapy plus a monoclonal antibody against HER2 for metastatic breast cancer that overexpresses HER2" The New England Journal of Medicine (2001) 344:783-792.

Sorlie, et al., "Gene expression patterns of breast carcinomas distinguish tumor subclasses with clinical implications" Proceedings of the National Academy of Sciences of the United States of America (2001) 98:10869-10874.

Sotiriou, et al. "Gene expression profiling in breast cancer: understanding the molecular basis of histologic grade to improve prognosis" Journal of the National Cancer Institute (2006) 98:262-272.

Strande, et al., "The proteome of the human breast cancer cell line MDA-MB-231: Analysis by LTQ-Orbitrap mass spectrometry" Proteomics Clinical applications (2009) 3:41-50.

Sutton, et al., "Quantitative proteomic profiling of matched normal and tumor breast tissues" Journal of Proteome Research (2010) 9:3891-3902.

Turashvili, et al. "Novel markers for differentiation of lobular and ductal invasive breast carcinomas by laser microdissection and microarray analysis" BMC cancer (2007) 7:55.

Uhlen, et al., "Towards a knowledge-based Human Protein Atlas" Nature Biotechnology (2010) 28:1248-1250.

Van De Vijver, et al., "A gene-expression signature as a predictor of survival in breast cancer" The New England Journal of Medicine (2002) 347:1999-2009.

Nang, et al., "Stress-induced phosphoprotein 1 as a secreted biomarker for human ovarian cancer promotes cancer ell proliferation" Molecular & Cellular Proteomics (2010) 9:1873-1884.

Wingren, et al., "Strategy for surveying the proteome using affinity proteomics and mass spectrometry" Proteomics (2009) 9:1511-1517.

Wirapati, et al., "Meta-analysis of gene expression profiles in breast cancer: toward a unified understanding of breast cancer subtyping and prognosis signatures" Breast Cancer Research (2008) 10:R65.

Yang, et al., "Proteomic Approach Reveals FKBP4 and S100A9 as Potential Prediction Markers of Therapeutic Response to Neoadjuvant Chemotherapy in Patients with Breast Cancer" Journal of Proteome Research (2011) 11: 1078-1088.

Zhang, et al., "Lactation defect with impaired secretory activation in AEBP1-null mice" PloS one (2011) 6:e27795.

(56) References Cited

OTHER PUBLICATIONS

Willet, et al., "Best practice diagnostic guidelines for patients presenting with breast symptoms guideline" (2010) Department of Health, United Kingdom; obtained at: http://www.associationofbreastsurgery.org.uk/media/4585/best_practice_diagnostic_guidelines_for_patients_presenting_with_breast_symptoms.pdf.
Opstal-Van Winden, et al., Searching for early breast cancer biomarkers by serum protein profiling of pre-diagnostic serum; a nested case-control study: BMC Cancer (2011) 11:381.
Dunn, et al., "Cancer immunoediting: from immunosurveillance to tumor escape" Nature Immunology (2002) 3 (11):991-8.
Burnet, M. "Cancer; a biological approach. I. The processes of control" British Medical Journal (1957) 1 (5022):779-86.
Dunn, et al., "Interferons, immunity and cancer immunoediting" Nature Reviews Immunology (2006) 6(11):836-48.
Shankaran, et al., "IFNgamma and lymphocytes prevent primary tumour development and shape tumour immunogenicity" Nature (2001) 410(6832):1107-11.
Dunn, et al., "The immunobiology of cancer immunosurveillance and immunoediting" Immunity (2004) 21(2):137-48.
Schreiber, et al., "Cancer immunoediting: integrating immunity's roles in cancer suppression and promotion" Science (2011) 331(6024):1565-70.
Koebel, et al., "Adaptive immunity maintains occult cancer in an equilibrium state" Nature (2007) 450(7171):903-7.
Mantovani, et al., "Cancer-related inflammation" Nature (2008) 454(7203):436-44.
Kraman, et al., "Suppression of antitumor immunity by stromal cells expressing fibroblast activation protein-alpha" Science (2010) 330(6005):827-30.
Teng, et al., "Immune-mediated dormancy: an equilibrium with cancer" Journal of Leukocyte Biology (2008) 84 (4):988-93.
Berglund, et al., "The Malmo Diet and Cancer Study. Design and feasibility" Journal of Internal Medicine (1993) 233 (1):45-51.
Manjer, et al., "The Malmo Diet and Cancer Study: representativity, cancer incidence and mortality in participants and non-participants" European Journal of Cancer Prevention (2001) 10(6):489-99.
Persson, et al., "Molecular Evolution of Specific Human Antibody against MUC1 Mucin Results in Improved Recognition of the Antigen on Tumor Cells" Tumor Biology (2009) 30(4):221-31.
Gustavsson, et al., "Surrogate antigens as targets for proteome-wide binder selection" New Biotechnology (2011) 28(4):302-11.
Carlsson, et al., "Serum Protein Profiling of Systemic Lupus Erythematosus and Systemic Sclerosis Using Recombinant Antibody Microarrays" Molecular & Cellular Proteomics (2011) 10(5):10.1074/mcp.M110.005033.
Dexlin-Mellby, et al., "Tissue proteome profiling of preeclamptic placenta using recombinant antibody microarrays" Proteomics (2010) 4(10-11):794-807.
Wu, et al., "The impact of centering first-level predictors on individual and contextual effects in multilevel data analysis" Nursing Research (2005) 54(3):212-6.
Chang, et al., "LIBSVM: a library for support vector machines" (2007) obtained at: http/::wwwcsientuedutw/cjlin/libsvm.
D'Cruz, et al., "Systemic lupus erythematosus" Lancet (2007) 369(9561):587-96.
Ross, et al., "Breast cancer biomarkers" Advances in Clinical Chemistry (2005) 40:99-125.
Nicolini, et al., "Cytokines in breast cancer" Cytokine & Growth Factor Reviews (2006) 17(5):325-37.
Hiu, et al., "Human body fluid proteome analysis" Proteomics (2006) 6(23):6326-53.
Levenson, V.V., "Biomarkers for early detection of breast cancer: what, when, and where?" Biochim Biophys Acta (2007) 1770(6):847-56.
Cho, W.C., "Contribution of oncoproteomics to cancer biomarker discovery" Mol. Cancer (2007) 6:25.
Kingsmore, S.F., "Multiplexed protein measurement: technologies and applications of protein and antibody arrays" Nat. Rev. Drug Discov. (2006) 5(4):310-20.
Wingren, et al., "Antibody microarrays: current status and key technological advances" Omics (2006) 10(3):411-27.
Pavlickova, et al., "Advances in recombinant antibody microarrays" Clin. Chim. Acta (2004) 343(1-2):17-35.
Orchekowski, et al., "Antibody microarray profiling reveals individual and combined serum proteins associated with pancreatic cancer" Cancer Res. (2005) 65(23):11193-202.
Knezevic, et al., "Proteomic profiling of the cancer microenvironment by antibody arrays" Proteomics (2001) 1 (10):1271-1278.
Miller, et al., "Antibody microarray profiling of human prostate cancer sera: antibody screening and identification of potential biomarkers" Proteomics (2003) 3(1):56-63.
Shafer, et al., "Antibody array profiling reveals serum TSP-1 as a marker to distinguish benign from malignant prostatic disease" Prostate (2007) 67(3):255-67.
Sreekumar, et al., "Profiling of cancer cells using protein microarrays: discovery of novel radiation-regulated proteins" Cancer Res. (2001) 61(20):7585-93.
Jain, K.K. "Personalised medicine for cancer: from drug development into clinical practice" Expert Opin. Pharmacother. (2005) 6(9):1463-76.
Louhimo, et al., "Combination of HCGbeta, CA 19-9 and CEA with logistic regression improves accuracy in gastrointestinal malignancies" Anticancer Res. (2002) 22(3):1759-64.
Matsuura, et al., "Increased level of circulating adhesion molecules in the sera of breast cancer patients with distant metastases" Jpn. J. Clin. Oncol. (1997) 27(3):135-9.
Burges, C.J.C., "A Tutorial on Support Vector Machines for Pattern Recognition" Data Mining and Knowledge Discovery (1998) 2:121-167.
Winter, et al., "Man-made antibodies" Nature (1991) 349(6307):293-9.
Collett, et al., "Production and processing of aptamer microarrays" Methods (2005) 37:4-15.
Carlsson, et al., "n-CoDeR concept: unique types of antibodies for diagnostic use and therapy" Expert Rev. Mol. Diagn. (2001) 1:102-108.
Clackson, et al., "Making antibody fragments using phage display libraries" Nature (1991) 352(6336):624-8.
Marks, et al. "By-passing immunization. Human antibodies from V-gene libraries displayed on phage" J. Mol. Biol. (1991) 222(3):581-97.
Smith, G.P. "Filamentous fusion phage: novel expression vectors that display cloned antigens on the virion surface" Science (1985) 228(4705):1315-7.
Santi, et al., "Bacteriophage Lambda Display of Complex cDNA Libraries: A New Approach to Functional Genomics" J Mol. Biol. (2000) 296:497-508.
Gunneriusson, et al., "Staphylococcal Surface Display of Immunoglobulin A (IgA)- and IgE-Specific In Vitro-Selected Binding Proteins (Affibodies) Based on Staphylococcus aureus Protein A" Applied Environmental Microbiol. (1999) 65:4134-4140.
Kenan, et al., "In Vitro Selection of Aptamers from RNA Libraries" Methods Mol. Biol. (1999) 118:217-31.
Kieke, et al., "Selection of functional T cell receptor mutants from a yeast surface-display library" Proc. Natl. Acad. Sci. (1999) 96:5651-5656.
Hanes, et al., "In vitro selection and evolution of functional proteins by using ribosome display" Proc. Natl. Acad. Sci. (1997) 94:4937-4942.
He, et al., "Antibody-ribosome-mRNA (ARM) complexes as efficient selection particles for in vitro display and evolution of antibody combining sites" Nucleic Acids Research (1997) 25(24):5132-5134.
Nemoto, et al. "In vitro virus: bonding of mRNA bearing puromycin at the 3'-terminal end to the C-terminal end of its encoded protein on the ribosome in vitro" FEBS Lett. (1997) 414(2):405-8.
Daugherty, et al., "Antibody affinity maturation using bacterial surface display" Protein Eng. (1998) 11(9):825-32.
Daugherty, et al., "Development of an optimized expression system for the screening of antibody libraries displayed on the *Escherichia coli* surface" Protein Eng. (1999) 12(7):613-21.

(56) References Cited

OTHER PUBLICATIONS

Shusta, et al., "Yeast Polypeptide Fusion Surface Display Levels Predict Thermal Stability and Soluble Secretion Efficiency" J. Mol. Biol. (1999) 292:949-956.

Morrison, et al. "Chimeric human antibody molecules: mouse antigen-binding domains with human constant region domains." Proc. Natl. Acad. Sci. (1984) 81(21):6851-5.

Better, et al. "*Escherichia coli* secretion of an active chimeric antibody fragment" Science (1988) 240(4855):1041-3.

Skerra, et al. "Assembly of a functional immunoglobulin Fv fragment in *Escherichia coli*" Science (1988) 240 (4855):1038-41.

Bird, et al. "Single-chain antigen-binding proteins" Science (1988) 242(4877):423-6.

Huston, et al., "Protein engineering of antibody binding sites: Recovery of specific activity in an anti-digoxin single-chain Fv analogue produced in *Escherichia coli*" Proc. Natl. Acad. Sci. (1988) 85:5879-5883.

Ward, et al. "Binding activities of a repertoire of single immunoglobulin variable domains secreted from *Escherichia coli*" Nature (1989) 341(6242):544-6.

Zola, H., "Monoclonal Antibodies: A manual of techniques" 1st ed. (1987) CRC Press, Boca Raton, Florida, pp. 17-61.

Hurrell, J.G.R., "Monoclonal Hybridoma Antibodies: Techniques and applications" (1982) CRC Press, Boca Raton, Florida, pp. 1-57.

Fraker, et al., "Protein and cell membrane iodinations with a sparingly soluble chloroamide, 1,3,4,6-tetrachloro-3a,6a-diphrenylglycoluril" Biochem. Biophys. Res. Commun. (1978) 80(4):849-57.

Jenkins, et al., "Arrays for protein expression profiling: Towards a viable alternative to two-dimensional gel electrophoresis?" Proteomics (2001) 1:13-29.

Lal, et al., "Antibody arrays: an embryonic but rapidly growing technology" Drug Discov. Today (2002) 7(18 Suppl):143-9.

Parkin, et al., "Global Cancer Statistics, 2002" CA Cancer J. Clin. (2005) 55:74-108.

Gonzalez-Angulo, et al., "Overview of Resistance to Systemic Therapy in Patients with Breast Cancer" Adv. Exp. Med. Biol. (2007) 608:1-22.

Eifel, et al., "National Institutes of Health Consensus Development Conference Statement: Adjuvant Therapy for Breast Cancer, Nov. 1-3, 2000" J. Natl. Cancer Inst. (2001) 93(13):979-989.

Goldhirsch, et al., "Thresholds for therapies: highlights of the St Gallen International Expert Consensus on the Primary Therapy of Early Breast Cancer 2009" Annals Oncol. (2009) 20:1319-1329.

Van'T Veer, et al., "Gene expression profiling predicts clinical outcome of breast cancer" Nature (2002) 415:530-536.

Paik, et al., "A multigene assay to predict recurrence of tamoxifen-treated, node-negative breast cancer" N. Engl. J. Med. (2004) 351:2817-2826.

Ingvarsson, et al., "Detection of pancreatic cancer using antibody microarray-based serum protein profiling" Proteomics (2008) 8:2211-2219.

Sanchez-Carbayo, et al., "Profiling Bladder Cancer Using Targeted Antibody Arrays" Am. J. Pathol. (2006) 168:93-103.

Ellmark, et al., "Identification of Protein Expression Signatures Associated with Helicobacter pylori Infection and Gastric Adenocarcinoma Using Recombinant Antibody Microarrays" Mol. Cell. Proteomics (2006) 5:1638-1646.

Wingren, et al., "Design of recombinant antibody microarrays for complex proteome analysis: Choice of sample labeling-tag and solid support" Proteomics (2007) 7:3055-3065.

Eden, et al., "'Good Old' clinical markers have similar power in breast cancer prognosis as microarray gene expression profilers" Eur. J. Cancer (2004) 40:1837-41.

Nimeus-Malmstrom, et al., "Gene expression profiling in primary breast cancer distinguishes patients developing local recurrence after breast-conservation surgery, with or without postoperative radiotherapy" Breast Cancer Res. (2008) 10:R34.

Chelinska, et al., "Systemic inflammation as a confounding factor in cancer biomarker discovery and validation" Nature (2010) 10:2-3.

Sharma, et al., "Early detection of breast cancer based on gene-expression patterns in peripheral blood" Breast Cancer Res. (2005) 7:R634-44.

Aebersold, et al., "Mass spectrometry-based proteomics" Nature (2003) 13:198-207.

Ekins, R.P. "Ligand assays: from electrophoresis to miniaturized microarrays" Clin. Chem. (1998) 44:2015-2030.

Zhu, et al., "Protein chip technology" Curr. Opin. Chem. Biol. (2003) 7:55-63.

Anderson, et al., "The human plasma proteome: history, character, and diagnostic prospects" Mol. Cell. Proteomics (2002)1:845-867.

Borrebaeck, et al., "Design of high-density antibody microarrays for disease proteomics: Key technological issues" J. Proteomics (2009) 72:928-935.

Steinhauer, et al., "Single framework recombinant antibody fragments designed for protein chip applications" Biotechniques (2002) 33:S38-S45.

Wingren, et al., "Microarrays based on affinity-tagged scFv antibodies: sensitive detection of analyte in complex proteomes" Proteomics (2005) 5:1281-1291.

Borrebaeck, et al., "High-throughput proteomics using antibody microarrays: an update" Expert Rev Mol Diagn. (2007) 7:673-686.

\* cited by examiner

METHOD, ARRAY AND USE THEREOF

This application a continuation application of U.S. patent application Ser. No. 13/702,756, filed Feb. 19, 2013, which is a § 371 application of PCT/GB2011/000865, filed on Jun. 9, 2011, which claims priority to GB 1009798.8, filed on Jun. 11, 2010. The entire disclosure of each of the foregoing applications is incorporated by reference herein.

FIELD OF INVENTION

The present invention relates to methods for the prognosis of breast cancer and biomarkers and arrays for use in the same.

BACKGROUND

Breast cancer is one of the most common tumor types in the Western world, affecting more than every tenth woman (1). One fourth of all malignant diagnoses are for breast cancer and since late 1990 the incidence worldwide, especially for the age group 45 to 70, has been increasing, although there has been a slight decline during the past few years. One explanation for the decrease is that early screening activities (mammography) and endocrine and cytostatic therapies have improved survival.

In spite of this decline, breast cancer still kills over one hundred women every day in the United States. Furthermore, despite improvements in early detection and understanding of the molecular basis of breast cancer, approximately 30% of all patients with primary breast cancer will develop distant recurrence of the disease (i.e. metastasis) (2).

Once metastatic disease develops, the possibility of a cure is very limited or non-existing. To offer better treatments with an increased efficacy and lower toxicity, therapies must be selected based on the clinical and molecular characteristics of the tumor. Today, there are only limited possibilities to predict disease outcome using traditional clinical predictors, such as histological grade and lymph node status (3, 4).

Recently, genomic studies have opened up the possibility to identify patients with poor prognosis regarding recurrence-free survival, using expression analysis of a multitude of different genes (5, 6). However, despite tremendous efforts it is presently not possible to perform risk assessments for breast cancer metastasis using a simple blood test, although recent developments in affinity proteomics have advanced the field of cancer biomarkers (7-9). Serum is a particularly valuable source, since it is not only useful for the initial screen of the disease but could also be used for continuous monitoring and analysis of therapy efficacy, which is in contrast to predictors based on measurements performed at the time of surgery.

Hence, there exists a need for improved methods for the prognosis of breast cancer and, in particular, the risk of developing distant recurrence of the disease (i.e. metastasis).

Against this background, the present inventors have now developed a proteomic, serum-based approach to prognosis breast cancer and identified a series of serum biomarkers for determining the risk of developing distant recurrence of the disease (i.e. metastasis).

SUMMARY OF THE INVENTION

Accordingly, in a first aspect, the invention provides a method for the prognosis of breast cancer in a subject comprising the steps of:

(a) providing a first proteome sample from the subject;
(b) measuring in the first proteome sample the amount of one or more biomarkers selected from the group of biomarkers listed in Table 1;
(c) providing an additional (e.g. a second) proteome sample from the subject;
(d) measuring in the additional proteome sample the amount of the one or more biomarkers selected from the group of biomarkers listed in Table 1 measured in step (b); and
(e) determining the difference between the amount of the one or more biomarkers in the first proteome sample and the additional proteome sample;
wherein the first proteome sample and additional proteome sample are representative of the proteome composition of the subject on different days, and wherein the difference between the amount of the one or more biomarkers in the first and additional (e.g. second) proteome samples is indicative of the risk of recurrence and/or metastasis of breast cancer in the subject.

By "the prognosis of breast cancer" we mean determining the risk of breast cancer recurrence in the subject. Such risk may be expressed as the probability of breast cancer recurrence within a specified time period, for example within one, two, three, four, five or ten years of the date of on which the prognosis is made.

It will be appreciated that the subject being tested in the method of the invention is typically human.

However, the methods may also be used for the prognosis of an animal such as a domestic or farm mammal (e.g. a horse, pig, cow, sheep, dog or cat).

Steps (a) and (c) of the method of the invention comprise providing first and additional proteome samples from a subject to be tested.

By "proteome sample" we mean a sample of the proteins expressed by the cells of the subject to be tested. The proteome sample may also include other biological molecules, or components or fragments thereof, the measurement of which can provide information useful in the prognosis of breast cancer. For example, the proteome sample may include protein or carbohydrate moieties, or antigenic components or fragments thereof.

In one embodiment, the proteome sample is a soluble proteome sample.

Preferably, the proteome samples provided in steps (a) and (c) are blood samples. In one embodiment, the blood sample(s) are unfractionated (i.e. the blood has not been separated into its component parts by centrifugation or any other means). In another embodiment the blood samples(s) are fractionated.

Thus, the proteome sample(s) may be serum or plasma or may be derived from serum or plasma.

Preferably, the proteome sample provided in steps (a) and/or (c) are serum or plasma samples, derived from blood samples taken from the subject to be tested.

The proteome samples provided in steps (a) and (c) may be prepared using methods well known in the art. It will be appreciated by persons skilled in the art that the sample may be in a native state or a digested format, depending on the method used to detect the proteins therein.

In one embodiment, the one or more of the samples collected from an individual are blood samples and the remainder are serum samples. However, it is preferred that the samples collected from the individual are either all blood samples or all serum samples.

The proteome samples provided in steps (a) and (c) are representative of the proteome composition of the subject. By "representative of the proteome composition of the subject" we mean that the proteome sample reflects the actual proteome composition of the subject at the time the sample was provided. The proteome sample may, for example, be a fluid or tissue sample taken directly from the subject or a processed derivative of such a sample.

The proteome samples provided in steps (a) and (c) are collected from the subject on different days and thus are representative of the proteome composition of the subject on different days. By "representative of the proteome composition of the subject on different days" we mean that each additional or further sample is representative of the proteome composition of the subject at a later time point than the previous proteome sample or samples provided.

In one embodiment, steps (c) and (d) are repeated in order to provide one or more further proteome samples from the subject and to measure therein the amount of the one or more biomarkers measured in step (b), wherein the one or more further proteome samples are representative of the proteome composition of the subject on different days from the first and additional proteome samples.

Thus, a plurality of additional proteome samples may be provided from the subject, e.g. third, fourth, fifth, sixth (and so on) proteome samples. It will be appreciated that the number of proteome samples provided from the subject may be sufficient to provide and/or confirm and/or monitor the prognosis of breast cancer.

In one embodiment, step (e) comprises determining the log change in biomarker amount between the first proteome sample and the additional proteome sample(s). The log change in the presence and/or amount of one or more biomarkers between the two or more proteome samples can be determined. This difference in biomarker amount over time is known as "biomarker velocity" and can be calculated using methods well known in the art (for example, see Makarov et al., 2009, *Ann. Rev. Med.*, 60:139-151).

Thus, biomarker velocity reflects the rate at which a biomarker's concentration (i.e. amount) changes over time rather than its absolute or static concentration/amount.

Steps (d) and (b) of the method of the invention comprise measuring in the proteome samples the amount of one or more biomarkers selected from the group of biomarkers listed in Table 1.

By "biomarker" we mean a naturally-occurring biological molecule, or component or fragment thereof, the measurement of which can provide information useful in the prognosis of breast cancer. For example, the biomarker may be a naturally-occurring protein or carbohydrate moiety, or an antigenic component or fragment thereof.

Accordingly, the amount of Apolipoprotein A4 (APOA4) may be measured. The amount of Apolipoprotein A4 (APOA4) may be measured.

The amount of Bruton's tyrosine kinase (BTK) may be measured. The amount of Complement-1 esterase inhibitor (C1 esterase inhibitor) may be measured. The amount of Complement factor B (Factor B) may be measured. The amount of CD40 may be measured. The amount of Homeodomain transcription factor CHX10 (CHX10) may be measured. The amount of Interleukin-1α (IL-1α) may be measured. The amount of Interleukin-5 (IL-5) may be measured. The amount of Interleukin-6 (IL-6) may be measured. The amount of Interleukin-7 (IL-7) may be measured. The amount of Interleukin-9 (IL-9) may be measured. The amount of Interleukin-12 (IL-12) may be measured. The amount of Interleukin-13 (IL-13) may be measured. The amount of Interleukin-18 (IL-18) may be measured. The amount of TBC1 domain family member 9 (KIAA0882) may be measured. The amount of Lewis$^x$/CD15 may be measured. The amount of Oxysterol binding protein-like 3 (OSBPL3) may be measured. The amount of Monocyte chemotactic protein-1 (MCP-1) may be measured. The amount of Sialyl Lewis$^x$ may be measured. The amount of Tumour necrosis factor-1 β (TNF-β) may be measured.

The amount of Integrin alpha-10 may be measured. The amount of β-galactosidase may be measured. The amount of CD40 ligand may be measured. The amount of Eotaxin may be measured. The amount of Glucagon-like peptide-1 receptor (GLP-1 R) may be measured. The amount of Interleukin-1β may be measured. The amount of Interleukin-3 may be measured. The amount of Interleukin-8 may be measured. The amount of Interleukin-10 may be measured. The amount of Interleukin-16 may be measured. The amount of MCP-4 may be measured. The amount of Myomesin-2 (MYOM2) may be measured. The amount of Rantes may be measured. The amount of Transforming growth factor-β (TGF-β1) may be measured. The amount of Regulator of nonsense transcripts 3B (UPF3B) may be measured. The amount of Interleukin-4 may be measured. The amount of Interleukin-1ra may be measured.

In one embodiment, step (b) and step (d) comprise measuring the amount of the each of the biomarkers listed in Table 1(A).

In another embodiment, step (b) and step (d) additionally or alternatively comprise measuring the amount of one or more biomarkers selected from the group listed in Table 1(B), for example 2, 3, 4, 5, 6, 7, 8, 9, 10, 11, 12, 13, 14, 15, 16, 17, 18 or all 19 of the biomarkers selected from the group listed in Table 1(B).

Thus, in one embodiment of the methods of the invention, the amount of all of the biomarkers listed in Table 1(A) and 1(B) is measured in step (b) and step (d).

In a further embodiment, step (b) and step (d) additionally or alternatively comprise measuring the amount of one or more of the biomarkers additionally or alternatively in Table 1(C), for example 2, 3, 4, 5, 6, 7, 8, 9, 10, 11, 12, 13, 14 or all 15 biomarkers additionally or alternatively in Table 1(C).

Thus, in one embodiment of the methods of the invention, the amount of all of the biomarkers listed in Table 1 is measured in step (b) and step (d).

Typically, step (b) and step (d) are performed using one or more first binding agents each capable of binding to a biomarker listed in Table 1. Typically, each first binding agent will be capable of binding specifically to a different biomarker from those listed in Table 1. However, it will be appreciated by persons skilled in the art that there may be some duplication in the biomarker to which the first binding agents bind. For example, two or more of the first binding agents may bind to different epitopes on the same biomarker (such duplication of target antigens may serve as a useful internal control for the methods of the invention, ensuring that the biomarker measurements are accurate).

Preferably, step (b) and step (d) are performed using two or more binding agents capable of binding a biomarker listed in Table 1. Where a biomarker listed in Table 1 is measured in step (b) and (d), it is preferred that such measurements are performed using a binding agent as defined in the Examples section (below). However, it will be appreciated that any other binding agent with specificity for the relevant biomarker may equally be used.

In one embodiment, in step (a) the first proteome sample from the subject is representative of the proteome composition of the subject within 4 weeks before or after tumour resection of the individual. Typically, the first proteome sample from the individual is representative of the proteome composition of the subject 4 weeks before tumour resection of the individual, for example, 3 weeks, 2 weeks, 1 week, 6 days, 5 days, 4 days, 3 days, 2 days, 1 day or 0 days before tumour resection of the individual. Preferably, the first proteome sample from the individual is representative of the proteome composition of the subject within 1 week before tumour resection of the individual. More preferably, the first proteome sample from the individual is representative of the proteome composition of the subject on the same day as tumour resection of the individual.

By "tumour resection" we mean surgical removal of the whole or part of a tumour. However, we also include any other main treatment approach. Depending on the stage and type of breast cancer, tumour resection may not be used as the main treatment approach or may be secondary to another therapeutic approach such as radiation therapy (i.e. radiotherapy), cryotherapy, photodynamic therapy, chemotherapy, hormone therapy and immunotherapy. In such cases, the initiation, completion or an intermediate period between initiation and completion of the main non-surgical therapy may be used as a reference point for collection of proteome samples of an individual.

Hence, by "before or after tumour resection of the individual" we also include before or after the initiation, completion or an intermediate period between initiation and completion of the main treatment approach as a possible reference point for collection of serum or plasma samples of an individual.

In one embodiment, the additional (e.g. second) proteome sample from the individual provided in step (c) is representative of the proteome composition of the subject at a time point within 3 to 9 months of tumour resection of the individual, for example within 4 to 8 months, within 5 to 7 months or at 6 months from tumour resection.

Thus, the additional proteome sample from the individual may be representative of the proteome composition of the subject within 40 weeks of tumour resection of the individual, for example within 39 weeks, 38 weeks, 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, 24 weeks, 23 weeks, 22 weeks, 21 weeks, 20 weeks, 19 weeks, 18 weeks, 17 weeks, 16 weeks, 15 weeks, 14 weeks, 13 weeks, 12 weeks, 11 weeks, 10 weeks, 9 weeks, 8 weeks, 7 weeks, 6 weeks, 5 weeks, 4 weeks, 3 weeks, 2 weeks, or 1 week after tumour resection of the individual. Typically, however, the additional proteome sample is representative of the proteome composition of the subject within 6 months of tumour resection of the individual.

Where steps (c) and (d) are repeated, the one or more further proteome sample or samples (i.e. third, fourth, fifth, sixth samples, and so on) are representative of the proteome composition of the subject at a regular anniversary of the tumour resection of the subject. Thus, the additional samples may be representative of the proteome composition of the subject at time intervals of every one month or more, for example every two months, three months, four months, five months, six months, seven months, eight months, nine months, ten months, eleven months, one year, two years, three years, five years or more after tumour resection. Typically, however, the one or more further proteome sample samples are representative of the proteome composition of the subject within 8 weeks before or after a yearly anniversary of the tumour resection, for example within about 7 weeks, 6 weeks, 4 weeks, 3 weeks, 2 weeks or 1 week before or after a yearly anniversary of the tumour resection of the individual.

Thus, it is preferred that the one or more further proteome sample or samples is/are representative of the proteome composition of the subject at or about a yearly anniversary of the tumour resection of the individual.

However, it will be appreciated that the further proteome sample or samples may be representative of the proteome composition of the subject at least 1 year following tumour resection in the individual, for example, at least 2 years, 3 years, 4 years, 5 years 6 years, 7 years, 8 years, 9 years or at least 10 years following tumour resection of the individual.

In one embodiment, the tumour resection is a primary breast cancer tumour resection. By "primary breast cancer" we mean the tumour is located in the organ or tissue where the cancer began.

In an alternative embodiment, the tumour resection is a secondary breast cancer tumour resection. By "secondary breast cancer" we mean that the tumour is located in another organ or tissue to where the cancer began (i.e. a metastatic tumour).

In a further embodiment, the subject is to be administered or has been administered chemotherapy and/or radiotherapy.

In one embodiment, steps (b) and (c) comprise continuous monitoring of the individual. By "continuous monitoring" we include routinely performing measurements on an uninterrupted, iterative basis (i.e. repeated measurements at regular short time intervals).

We also include performing measurements on an uninterrupted, non-iterative basis (i.e. real-time measurements). Continuous monitoring may be performed manually, but is preferably performed by an automated (e.g. computer-based) system.

In one embodiment, the risk of recurrence of breast cancer in an individual is determined as a numerical probability of breast cancer recurrence, for example as a percentage probability of breast cancer recurrence within a given time period.

However, in an alternative embodiment the risk of breast cancer in an individual is determined as either high risk or low risk. Hence, the individual to be tested will be placed in a "high risk" or "low risk" group with respect to breast cancer recurrence (i.e. metastasis).

By "high risk" we mean the individual has at least a 72% chance of breast cancer recurring with 3 years of tumour resection of the individual (in particular, of primary tumour resection of the individual). For example, the individual may have a 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or a 100% chance of breast cancer recurring with 3 years of tumour resection of the individual. By "low risk" we mean the individual has at most a 15% chance of breast cancer recurring with 3 years of tumour resection of the individual (in particular, of primary tumour resection of the individual). For example, the individual may have a 14%, 13%, 12%, 11%, 10%, 9%, 8%, 7%, 6%, 5%, 4%, 3%, 2%, 1%, 0.5%, 0.25%, 0.1%, 0.01% or a 0% chance of breast cancer recurring with 3 years of tumour resection of the individual.

Generally, the risk of recurrence of breast cancer in an individual is determined with an ROC AUC of at least 0.55, for example with an ROC AUC of at least, 0.60, 0.65, 0.70, 0.75, 0.80, 0.85, 0.90, 0.95, 0.96, 0.97, 0.98 or with an ROC AUC of at least 0.99. Preferably, the risk of recurrence of breast cancer in an individual is determined with an ROC AUC of at least 0.85.

Typically, the risk of recurrence of breast cancer in an individual is determined using a support vector machine (SVM), such as those available from http://cran.r-project.org/web/packages/e1071/index.html (e.g. e1071 1.5-24). However, any other suitable means may also be used.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training datapoints of any class (so-called functional margin), since in general the larger the margin the lower the generalization error of the classifier. For more information on SVMs, see for example, Burges, 1998, *Data Mining and Knowledge Discovery*, 2:121-167.

In one embodiment of the invention, the SVM is 'trained' prior to performing the methods of the invention using proteome samples from subjects assigned to known patient groups (namely, those patients in which breast cancer did not recur over a given time period and those patients in which breast cancer did recur over the given time period). By running such training samples, the SVM is able to learn what biomarker profiles are associated with a risk of recurrence of breast cancer. Once the training process is complete, the SVM is then able whether or not the proteome sample tested is from a subject who is at risk of breast cancer recurrence.

However, this training procedure can be by-passed by pre-programming the SVM with the necessary training parameters. For example, the risk of recurrence of breast cancer in a subject can be determined according to the known SVM parameters detailed in Table 2, based on the measurement of all the biomarkers listed in Table 1(A) and 1(B).

It will be appreciated by skilled persons that suitable SVM parameters can be determined for any combination of the biomarkers listed Table 1 by training an SVM machine with the appropriate selection of data (i.e. biomarker measurements in proteome samples from known patient groups.

In one embodiment, the risk of breast cancer recurrence is determined in combination with at least one other method of determining the risk of breast cancer recurrence such as in combination with one or more nucleic acid expression profiles associated with the risk of breast cancer recurrence. For example, the nucleic acid expression profile as defined in van't Veer et al., 2002, *Nature*, 415:530-536 and/or Paik et al., 2004, *N. Engl. J. Med.*, 351:2817-2826 may be used.

Alternatively or additionally, the risk of breast cancer recurrence may be determined in combination with conventional clinical markers. By "conventional clinical markers" we mean the stratification of patients into different prognostic groups based on clinical features such as menopausal status, oestrogen receptor status, progesterone status, ductal/lobular type, tumour size, lymph node stage/status and histological grade (as opposed to the expression of complex expression signatures). One common example of a prognostic index using conventional clinical markers is the Nottingham Prognostic Index (NPI) which was derived from a retrospective multivariate study, that is (to some degree) able to predict survival in patients with breast cancer. For more information, see for example, Edén et al., 2004, *European Journal of Cancer*, 40(12):1837-1841.

In a further embodiment, the one or more binding agents capable of binding a biomarker defined in Table 1 comprise or consist of an antibody or an antigen-binding fragment thereof. Preferably, the antibody or antigen-binding fragment thereof is a monoclonal antibody or a fragment thereof. More preferably, the antibody or antigen-binding fragment thereof is a recombinant antibody or antigen-binding fragment thereof.

The term "antibody" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecules capable of binding to an antigen in an immunoassay format that is known to those skilled in the art.

We also include the use of antibody-like binding agents, such as affibodies and aptamers.

Methods for obtaining antibodies, or antigen-binding fragments or derivatives thereof, with specificity to a given antigen (such as the biomarkers in Table 1) are well known in the art. A general review of the techniques involved in the synthesis of antibody fragments which retain their specific binding sites is to be found in Winter & Milstein (1991) *Nature* 349, 293-299.

Additionally, or alternatively, one or more of the first binding molecules may be an aptamer (see Collett et al., 2005, *Methods* 37:4-15).

Conveniently, an antibody library (such as the n-CoDeR library of BioInvent International AB; see Carlsson & Söderlind, 2001, *Expert Rev Mol Diagn.* 1:102-8) is screened to identify antibodies, or antigen-binding fragments or derivatives thereof, with desired binding specificities. Thus, molecular libraries such as antibody libraries (Clackson et al, 1991, *Nature* 352, 624-628; Marks et al, 1991, *J Mol Biol* 222(3): 581-97), peptide libraries (Smith, 1985, Science 228(4705): 1315-7), expressed cDNA libraries (Santi et al (2000) *J Mol Biol* 296(2): 497-508), libraries on other scaffolds than the antibody framework such as affibodies (Gunneriusson et al, 1999, *Appl Environ Microbiol* 65(9): 4134-40) or libraries based on aptamers (Kenan et al, 1999, *Methods Mol Biol* 118, 217-31) may be used as a source from which binding molecules that are specific for a given motif are selected for use in the methods of the invention.

The molecular libraries may be expressed in vivo in prokaryotic cells (Clackson et al, 1991, op. cit.; Marks et al, 1991, op. cit.) or eukaryotic cells (Kieke et al, 1999, *Proc Natl Acad Sci USA*, 96(10):5651-6) or may be expressed in vitro without involvement of cells (Hanes & Pluckthun, 1997, *Proc Natl Acad Sci USA* 94(10):4937-42; He & Taussig, 1997, *Nucleic Acids Res* 25(24):5132-4; Nemoto et al, 1997, *FEBS Lett*, 414(2):405-8).

In cases where protein-based libraries are used, the genes encoding the libraries of potential binding molecules are often packaged in viruses and the potential binding molecule displayed at the surface of the virus (Clackson et al, 1991, supra; Marks et al, 1991, supra; Smith, 1985, supra).

Perhaps the most commonly used display system is filamentous bacteriophage displaying antibody fragments at their surfaces, the antibody fragments being expressed as a fusion to the minor coat protein of the bacteriophage (Clackson et al, 1991, supra; Marks et al, 1991, supra). However, other suitable systems for display include using other viruses (EP 39578), bacteria (Gunneriusson et al, 1999, supra; Daugherty et al, 1998, *Protein Eng* 11(9):825-32; Daugherty et al, 1999, *Protein Eng* 12(7):613-21), and yeast (Shusta et al, 1999, *J Mol Biol* 292(5):949-56).

In addition, display systems have been developed utilising linkage of the polypeptide product to its encoding mRNA in so-called ribosome display systems (Hanes & Pluckthun, 1997, supra; He & Taussig, 1997, supra; Nemoto et al, 1997, supra), or alternatively linkage of the polypeptide product to the encoding DNA (see U.S. Pat. No. 5,856,090 and WO 98/37186).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

Thus, the antibody or antigen-binding fragment may be selected from the group consisting of intact antibodies, Fv fragments (e.g. single chain Fv [scFv] and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

By "scFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

When potential binding molecules are selected from libraries, one or more selector peptides having defined motifs are usually employed. Amino acid residues that provide structure, decreasing flexibility in the peptide or charged, polar or hydrophobic side chains allowing interaction with the binding molecule may be used in the design of motifs for selector peptides. For example:

(i) Proline may stabilise a peptide structure as its side chain is bound both to the alpha carbon as well as the nitrogen;
(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically, selection of binding molecules may involve the use of array technologies and systems to analyse binding to spots corresponding to types of binding molecules.

Hence, it will be appreciated that the antibody or antigen-binding fragment may be selected from the group consisting of intact antibodies, Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (e.g. dAbs, including single and dual formats (i.e. dAb-linker-dAb)).

Alternatively, a first binding agent may comprise or consist of antibody-like binding agents, for example affibodies or aptamers.

In one embodiment, the one or more biomarkers selected from the group defined in Table 1 are labelled with a detectable moiety. Preferably, all of the organic molecules of the sample are labelled with a detectable molecule.

By a "detectable moiety" we include a moiety which permits its presence and/or relative amount and/or location (for example, the location on an array) to be determined, either directly or indirectly. Suitable detectable moieties are well known in the art. Preferably, the detectable moiety is selected from the group consisting of a fluorescent moiety; a luminescent moiety; a chemiluminescent moiety; a radioactive moiety; an enzymatic moiety, a ligand moiety or a ligand binding moiety.

For example, the detectable moiety may be a fluorescent and/or luminescent and/or chemiluminescent moiety which, when exposed to specific conditions, may be detected. Such a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

In a further embodiment, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $^{17}$O, gadolinium, manganese or iron. Clearly, the agent to be detected (such as, for example, the one or more proteins in the test sample and/or control sample described herein and/or an antibody molecule for use in detecting a selected protein) must have sufficient of the appropriate atomic isotopes in order for the detectable moiety to be readily detectable.

The radio- or other labels may be incorporated into the proteins present in the samples of the methods of the invention and/or the binding agents of the invention in known ways. For example, if the binding agent is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

It will be appreciated by persons skilled in the art that proteins in the sample(s) to be tested may be labelled with a moiety which indirectly assists with determining the presence, amount and/or location of said proteins. Thus, the moiety may constitute one component of a multicomponent detectable moiety. For example, the proteins in the sample(s) to be tested may be labelled with biotin, which allows their subsequent detection using streptavidin fused or otherwise joined to a detectable label.

In a further embodiment step (b) and/or step (d) is performed using an array.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. Alternatively, affinity coupling of the probes via affinity-tags or similar constructs may be employed. By using well-known techniques, such as contact or non-contact printing, masking or photolithography, the location of each spot can be defined. For reviews see Jenkins, R. E., Pennington, S. R. (2001, *Proteomics,* 2, 13-29) and Lal et al (2002, *Drug Discov Today* 15; 7(18 Suppl):S143-9).

The array may be a bead-based array. Typically, the array is a surface-based array, for example a macroarray, microarray or nanoarray, preferably an antibody array or an antibody microarray.

Typically the array is a microarray. By "microarray" we include the meaning of an array of regions having a density of discrete regions of at least about 100/cm$^2$, and preferably at least about 1000/cm$^2$. The regions in a microarray have typical dimensions, e.g. diameter, in the range of between about 10-250 μm, and are separated from other regions in the array by about the same distance. The array may alternatively be a macroarray or a nanoarray.

Once suitable binding molecules (discussed above) have been identified and isolated, the skilled person can manufacture an array using methods well known in the art of molecular biology; see Examples below.

In a still further embodiment step (b) and/or step (d) is performed using an assay comprising a second binding agent capable of binding to the one or more first binding agent, the second binding agent having a detectable moiety. Suitable second binding agents are described in detail above in relation to the first binding agents.

Thus, the proteins of interest in the sample to be tested may first be isolated and/or immobilised using the first binding agent, after which the presence and/or relative amount of said proteins may be determined using a second binding agent.

Preferably, the second binding agent is an antibody or an antigen-binding fragment thereof. Conveniently, the antibody or fragment thereof is selected from the group consisting of: scFv; Fab; a binding domain of an immunoglobulin molecule. Suitable antibodies and fragments, and methods for making the same, are described in detail above.

Alternatively, the second binding agent may be an antibody-like binding agent, such as an affibody or aptamer.

Alternatively, where the detectable moiety on the protein in the sample to be tested comprises or consists of a member of a specific binding pair (e.g. biotin), the second binding agent may comprise or consist of the complimentary member of the specific binding pair (e.g. streptavidin).

Where a detection assay is used, it is preferred that the detectable moiety is selected from the group consisting of: a fluorescent moiety; a luminescent moiety; a chemiluminescent moiety; a radioactive moiety; an enzymatic moiety, a ligand moiety or a ligand binding moiety. Examples of suitable detectable moieties for use in the methods of the invention are described above.

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Thus, in one embodiment the assay is an ELISA (Enzyme Linked Immunosorbent Assay) which typically involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemiluminescent systems based on enzymes such as luciferase can also be used.

Conjugation with the vitamin biotin is frequently used since this can readily be detected by its reaction with enzyme-linked avidin or streptavidin to which it binds with great specificity and affinity.

In an alternative embodiment, the assay used for protein detection is conveniently a fluorometric assay. Thus, the detectable moiety of the second binding agent may be a fluorescent moiety, such as an Alexa fluorophore (for example Alexa-647).

Preferably, the antibody or antigen-binding fragment thereof is a recombinant antibody or antigen-binding fragment thereof.

In one embodiment the method of the first aspect of the invention is an in vitro method. In an alternative embodiment, the method of the first aspect of the invention is an in vivo method.

A second aspect of the invention provides an array for use in a method according to the first aspect of the invention, the array comprising one or more first binding agents as defined above. Preferably, the array comprises one or more binding agents capable of binding to a biomarker in Table. More preferably, the array comprises binding agents capable of binding to a biomarker in Table 1(A), most preferably, to all of the biomarkers in Table 1(a).

The array may additionally or alternatively comprise one or more binding agents capable of binding to a biomarker in Table 1(B), for example, 2, 3, 4, 5, 6, 7, 8, 9, 10, 11, 12, 13, 14, 15, 16, 17, 18 or 19 of the biomarkers in Table 1(B). Hence, it is preferred that the array comprises binding agents capable of binding to each of the biomarkers defined in Table 1(A) and Table 1(B).

In addition, the array may comprise binding agents capable of binding to one or more of the biomarkers defined in Table 1(C), for example, to 2, 3, 4, 5, 6, 7, 8, 9, 10, 11, 12, 13, 14 or 15 of the biomarkers in Table 1(C). Preferably, the array comprises binding agents capable of binding to each of the biomarkers defined in Table 1(C).

It will be appreciated by persons skilled in the art that the array may comprise a plurality of different binding agents capable of binding to the same biomarker selected from the above groups of biomarkers.

In one embodiment, the binding agents comprise or consist of an antibody or antigen-binding fragment thereof, such as a monoclonal antibody or a fragment thereof. The antibody or antigen-binding fragment thereof may be a recombinant antibody or antigen-binding fragment thereof.

The antibody or antigen-binding fragment may be selected from the group consisting of intact antibodies, Fv fragments (e.g. single chain Fv and disulphide-bonded Fv), Fab-like fragments (e.g. Fab fragments, Fab' fragments and F(ab)$_2$ fragments), single variable domains (e.g. V$_H$ and V$_L$ domains) and domain antibodies (e.g. dAbs, including single and dual formats, i.e. dAb-linker-dAb). Preferably, the antibody or antigen-binding fragment is a single chain Fv (scFv).

Alternatively, the binding agent may comprise or consist of an antibody-like binding agent, for example an affibody or aptamer.

In one embodiment the binding agents are immobilised. However, they may alternatively be non-fixed.

In another embodiment, the array comprises or consists of at least 2 to 10 different binding agents (e.g. different antibodies) for each of the biomarkers listed in Table 1(A) and/or 1(B) and/or 1(C), for example at least 2-3, 2-4, 2-5, 2-6, 2-7, 2-8, or 2-9 different binding agent species for each biomarker. Thus, the array may comprise or consist of at least 3 different binding agents for each biomarker.

Arrays suitable for use in the methods of the invention are discussed in detail above.

A third aspect of the invention provides the in vitro use of a biomarker selected from the group of biomarkers in Table 1(A) as a prognostic marker for determining risk of recurrence and/or metastasis of breast cancer in a subject. In one embodiment, the biomarker(s) is/are for use in combination with one or more additional biomarkers selected from the group of biomarkers in Table 1(B) and/or 1(C). The use may be in combination with all of the biomarkers from (i) Table 1(A) and/Table 1(B); (ii) Table 1(A) and Table 1(C); (iii) Table 1(B) and Table 1(C); (iv) Table 1(A), Table 1(B) and Table 1(C), or example, 1 or 2 of the biomarkers from Table 1(A), 1, 2, 3, 4, 5, 6, 7, 8, 9, 10, 11, 12, 13, 14, 15, 16, 17, 18 or 19 of the biomarkers from Table 1(B) and/or, 1, 2, 3, 4, 5, 6, 7, 8, 9, 10, 11, 12, 13, 14 or 15 of the biomarkers from Table 1(C).

Conveniently, the use comprises or consists of 3 or more biomarkers selected from the group defined in Table 1, for example, at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 biomarkers selected from the group defined in Table 1. It is preferred that the use comprises or consists of biomarkers comprising the group Apolipoprotein A4 (APOA4), ATP synthase subunit beta, mitochondrial (ATP5B), Bruton's tyrosine kinase (BTK), Complement-1 esterase inhibitor (C1 esterase inhibitor), Complement factor B (Factor B), CD40, Homeodomain transcription factor CHX10 (CHX10), Interleukin-1α (IL-1α), Interleukin-5 (IL-5), Interleukin-6 (IL-6), Interleukin-7 (IL-7), Interleukin-9 (IL-9), Interleukin-12 (IL-12), Interleukin-13 (IL-13), Interleukin-18 (IL-18), TBC1 domain family member 9 (KIAA0882), Lewis$^x$/CD15, Oxysterol binding protein-like 3 (OSBPL3), Monocyte chemotactic protein-1 (MCP-1), Sialyl Lewis$^x$, Tumour necrosis factor-1 β (TNF-β).

A fourth aspect of the invention provides a kit for determining the risk of recurrence of breast cancer in an individual comprising or consisting of:
(i) one or more binding agents capable of binding to a biomarker listed in Table 1(A) and/or 1(B) and/or 1(C); and
(ii) instructions for performing the method of the invention.

In one embodiment, the kit further comprises one or more second binding agents as defined above. Preferably the kit also comprises or consists of:
(iii) An array according the third aspect of the invention; and
(iv) instructions for performing the method of the invention.

In one embodiment, the kit comprises binding agents capable of binding to each of the biomarkers defined in Table 1(A) and/or 1(B) and may additionally comprise binding agents capable of binding to one or more of the biomarkers defined in Table 1(C).

Alternatively, the kit may comprise a plurality of different binding agents capable of binding to the same biomarker selected from the group of biomarkers in Table 1(A) and/or 1(B) and/or 1(C).

In one embodiment, the binding agents comprise or consist of an antibody or antigen-binding fragment thereof such as a monoclonal antibody or a fragment thereof. Preferably the antibody or antigen-binding fragment thereof is a recombinant antibody or antigen-binding fragment thereof.

Figure 1B:
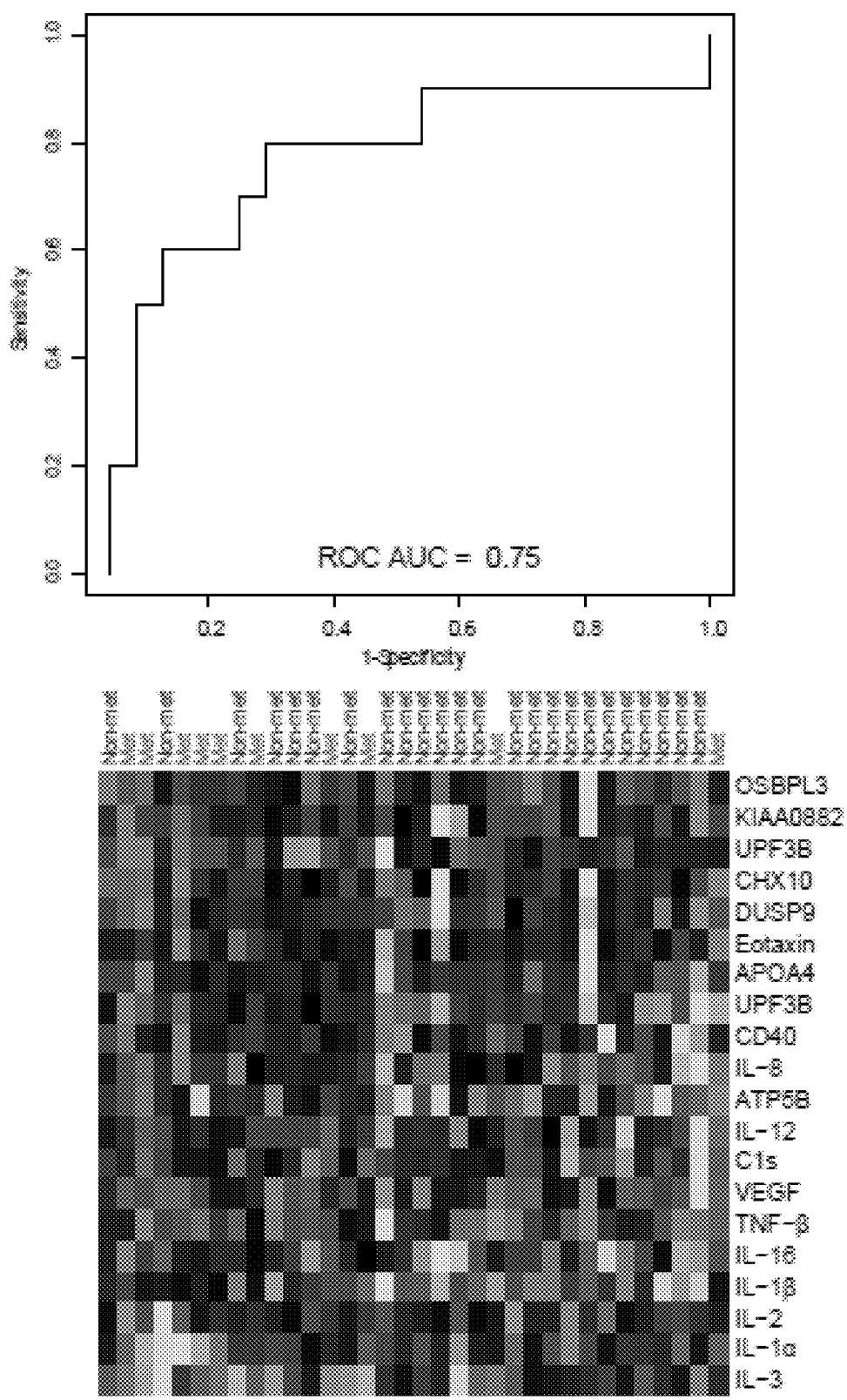

Preferred, non-limiting examples which embody certain aspects of the invention will now be described, with reference to the following figures:

FIGS. 1A and 1B: SVM analysis for prediction of metastatic breast cancer. FIG. 1A: Analyte levels for samples collected at 3-6 months after surgery were compared to the samples taken at the time of surgery. The differences in all analytes as identified on the arrays were fed to an SVM, which, using a leave-one-out cross-validation procedure, was trained to classify the patient as one that will develop metastatic cancer or one who will not. The analysis yielded a ROC AUC of 0.88. In the heat map all analytes displaying a Wilcoxon p-value of <0.05 are shown, with red meaning increase and green decrease, regarding biomarker velocity. FIG. 1B: The same SVM analysis, but using analyte velocity comparing samples taken at the time of surgery to samples taken 12 months after surgery. This analysis resulted in a ROC AUC of 0.75.

Figure 2A:
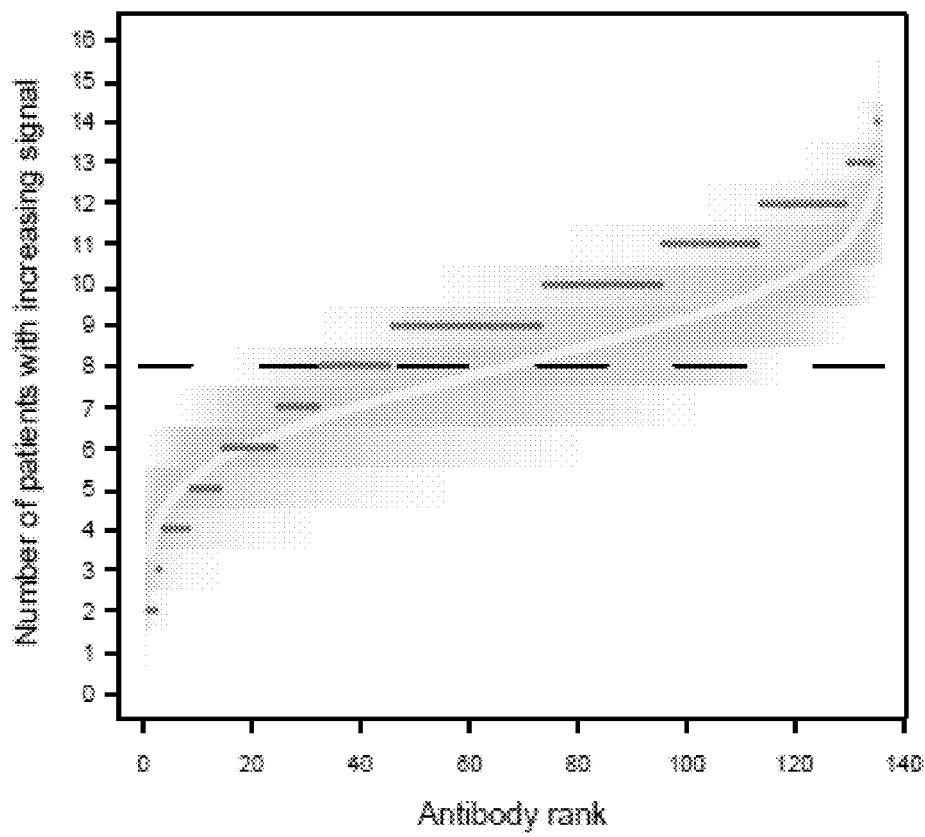

FIGS. 2A-2D: Analysis of false discovery rate and analyte velocity. FIG. 2A: The number of patients with higher biomarker signal for the second sample was identified for each antibody. The antibodies was sorted accordingly and plotted (red), with the antibody with increasing signal in the fewest patients to the left. The first and second sample was then randomly recombined, treating the second sample as the first and vice versa for a random set of patients. The number of patients with higher signal in the "second" sample was again identified, to achieve an estimation of the false positive rate (FPR) of the analysis. This procedure was repeated 10,000 times. The blue color describes how common a certain number of patients with increasing signal were for each antibody rank during the permutation of the randomly recombined dataset; white indicated non-existing and dark-blue the most common. The average value for each antibody rank is plotted as a yellow line. From this analysis it is evident that the true combination of the first and second sample gives a result that clearly diverges from the yellow line describing the FPR, not only in the tails of the plot, but even more so in the middle, indicating a general up-regulation. Plots showing the velocity for, (FIG. 2B) Lewis x; (FIG. 2C) IL-16; and (FIG. 2D) CD40, during the first 3-6 months after surgery, respectively. The signal velocity for these analytes was clearly positive for patients eventually developing metastatic breast cancer.

Figure 3A:
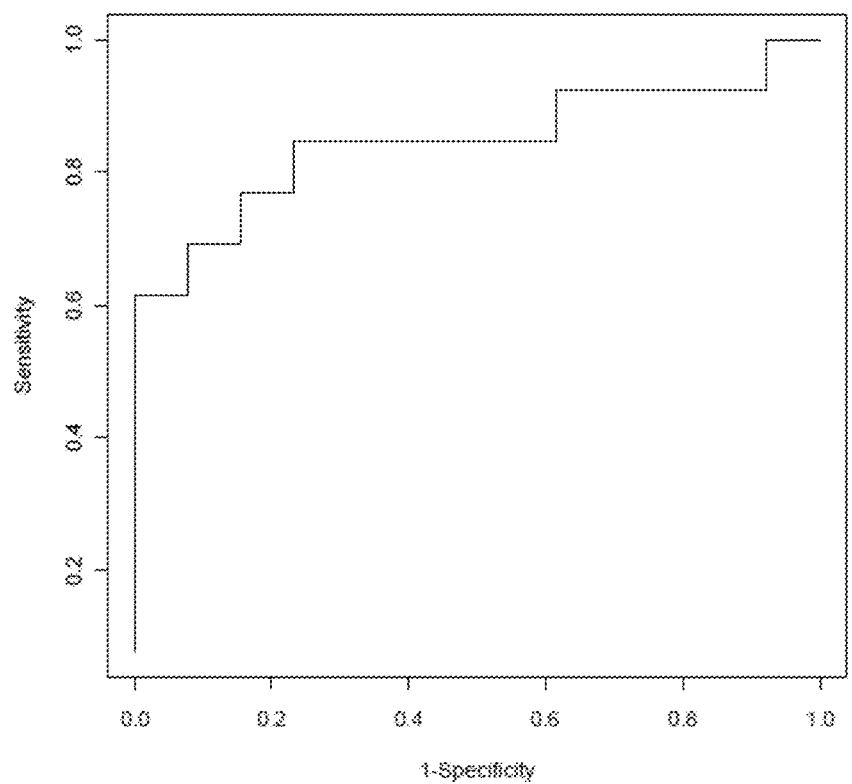
Figure 3B:
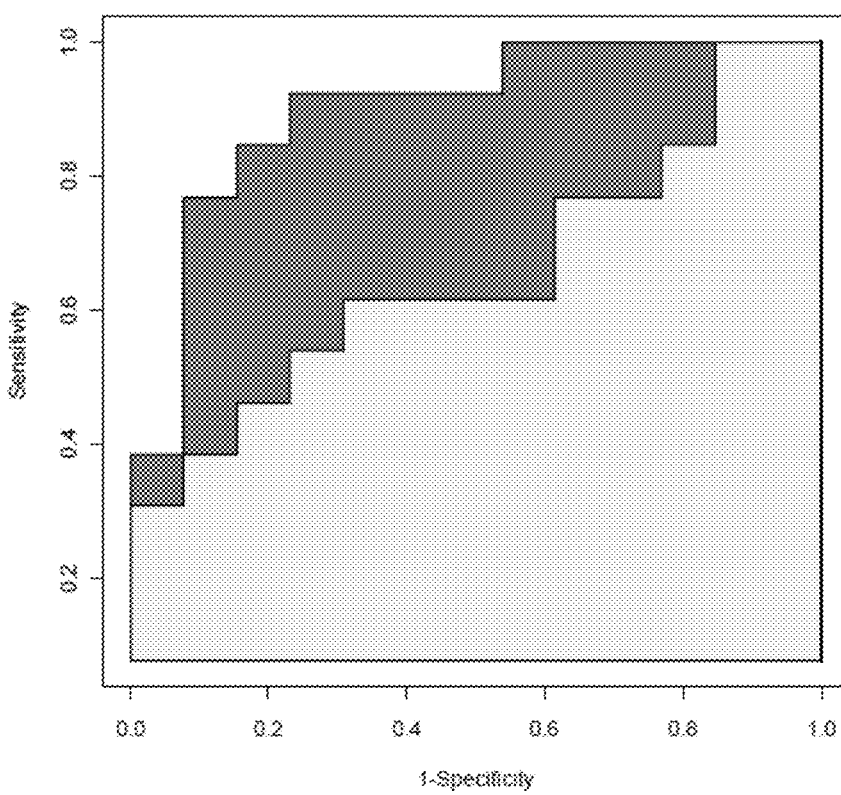

FIGS. 3A and 3B: Pre-validation of classification of patients into high or low risk for breast cancer reoccurrence. An SVM was trained on the discovery dataset and tested on the pre-validation dataset, using (FIG. 3A) Antibody array data derived from the 21 biomarker signature generated, using backward elimination, as described in the Supplementary Materials and Methods. The ROC AUC for this classification was 0.85; (FIG. 3B) An SVM was trained using conventional clinical data (yellow) giving a ROC AUC=0.66, whereas the combination of the 21 biomarker signature and conventional clinical parameters (red) resulted in a ROC AUC=0.90, demonstrating the added value in the array data.

Figure 4:
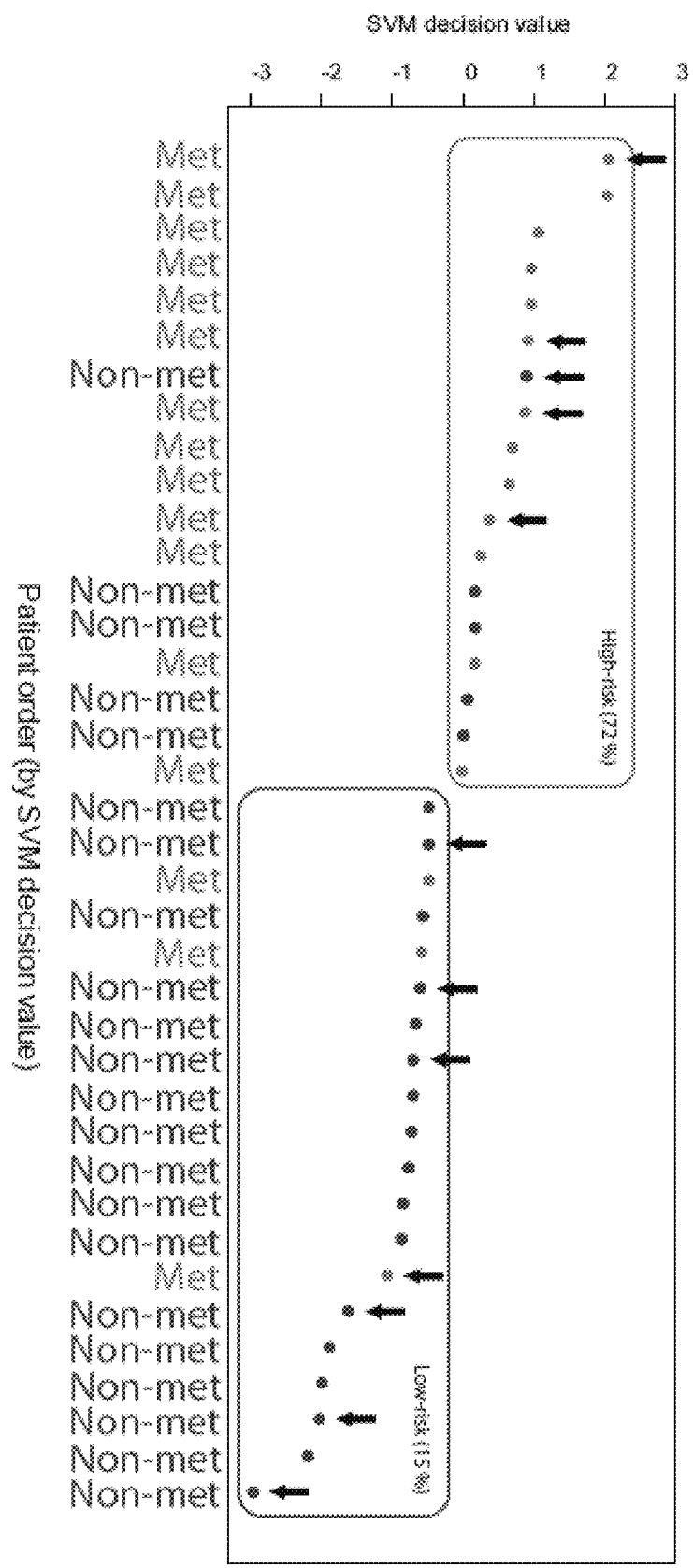

FIG. 4: Chemotherapy was found not to be a confounding factor for our candidate biomarker signature. The SVM decision values for all the patients are plotted and patients receiving chemotherapy during the first 3-6 months are indicated by arrows. When dividing the patients in to risk groups based on the SVM decision value, 72% of patients in the high-risk group (red) later developed metastasis, and only 15% in the low-risk group (blue). When correlating the result to which patients that was given adjuvant treatment (black arrows), it was evident that this factor did not bias the analysis, with 5/18 and 7/20 in the high- and low-risk group, respectively.

Figure 5:
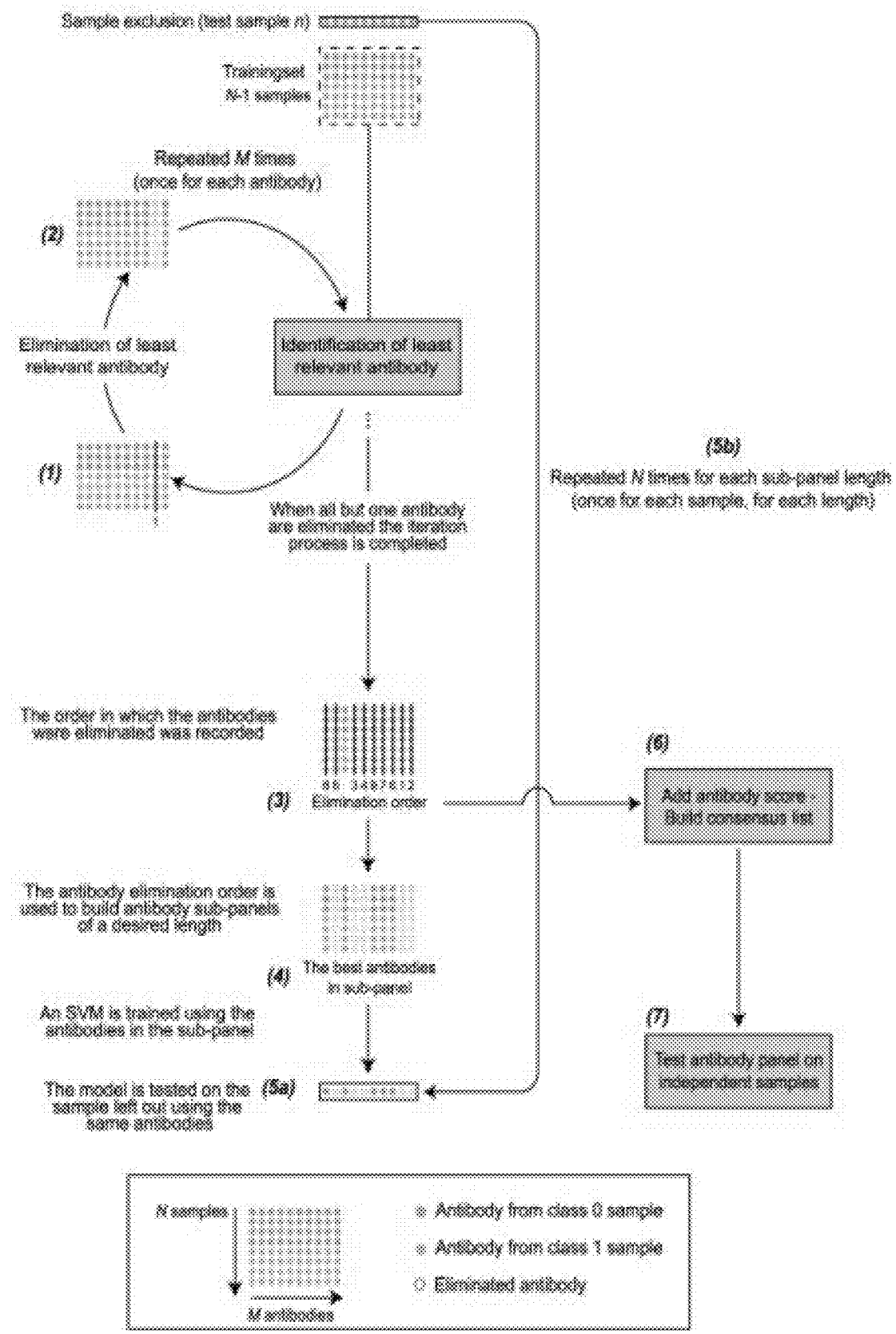

FIG. 5: Backward variable elimination. In order to reduce the number of antibodies used for the classification we combined the above leave-one-out procedure with a backward elimination process for the antibodies. This process also produced a ranking of the antibodies allowing low ranks to be assigned to randomly correlated antibodies.

EXAMPLES

Introduction

In order to define predictive serum biomarkers associated with tumor relapse in breast cancer, we hypothesized that decoding patterns of low-abundant immunoregulatory serum proteins could reveal important information about the risk of recurrence.

Consequently, utilizing state-of-the art recombinant antibody array technology capable of analyzing large numbers of low-abundant protein analytes, using only minute amounts of non-fractionated serum (10), we screened patient samples collected over a three year-period. The samples were collected from breast cancer patients before resection of the primary tumor and then every 6-12 months, resulting in up to 5 samples/patient. By analyzing the velocity, i.e. change over time, of the markers, information indicative of the patients risk to develop metastasis could be extracted.

This study demonstrates, for the first time, that a simple blood sample harbors predictive information of systemic tumor recurrence in breast cancer patients, which could allow for new possibilities in therapy selection. Furthermore, in terms of performance, it brings substantial added value to clinical predictors derived at the time of primary surgery.

Materials & Methods

Samples and Array Analysis

Serum samples were collected from two independent cohorts of patients, denoted as the discovery cohort and the pre-validation cohort (Table 3). In the discovery cohort, samples were collected from 38 patients diagnosed with primary breast cancer. Written informed consents were collected during the pre-operative visit at the Department of Surgery (Lund University Hospital, Lund), when also the serum samples were collected. Time and date were recorded when the blood samples were drawn. Serum were stored at −80° C., labeled with serial codes to enable blinded analyses. For the majority of the patients, the preoperative visit took place less than a week before the surgery. Blood was drawn a second time at the first follow-up (3-6 months) and then approximately every 12 months for three years. This study was approved by the Regional Ethical Committee (Lund, Sweden). In the pre-validation cohort, serum samples were drawn, as described for the discovery cohort, from 26 new and independent breast cancer patients. The patients that did not develop distant recurrence were followed up to 7 years (Table 3).

The recombinant antibody microarray platform contained 135 antibodies against 65 different antigens, i.e. for quality assurance we utilized 2-5 different antibody clones against the majority of antigens (Table 4). The microarray analysis, including sample preparation, antibody production, array fabrication and normalization, is described in detail (10, 11).

To be able to compare the prediction for distant recurrence, using conventional clinical parameters, we assigned each of the available parameters with numeric values, where premenopausal/postmenopausal status, ER & PgR-negative/positive, ductal/lobular type, and lymphnode status were set to −1 or 1, respectively. Furthermore, histological grade I, II or III was set to −1, 0 or 1, whereas the tumor size was continuously graded from −1 to 1. A support vector machine (SVM) was then trained on the discovery dataset, using either the conventional clinical data, or a combination of the clinical and microarray data.

Data Analysis Using the Support Vector Machine

A SVM was employed to classify the samples as belonging to one of two defined groups, using a linear kernel with the cost of constraints set to 1. No attempts were made to tune it in order to avoid the risk of over-fitting. The log differences between signals for samples collected at the time of operation and between three to six months later was calculated for each patient, and used to train and test the SVM classifier, using leave-one-out cross-validation. This training part, using the discovery cohort, included the creation of an antibody sub-panel by selecting antibodies that, in the training-set, displayed the highest combined discriminatory power. This selection of antibodies was made, using a cross-validated backward elimination strategy. Using this approach, we compiled a list of 21 antibodies with the highest scores (Table 1(A) and (B)) and trained a final SVM model, now termed frozen. The SVM parameters derived from the training are shown in Table 2.

During the pre-validation, serum samples from 26 new independent breast cancer patients (pre-validation cohort) were analyzed and tested, using the analyte velocities in the previously frozen SVM classifier.

Sample Preparation

The serum samples were biotinylated, using a protocol previously optimized for labeling the serum proteome (10). All serum samples were labeled, using EZ-Link Sulfo-NHS-LC-Biotin (Pierce, Rockford, Ill., USA), as previously described (10). Briefly, 50 µl serum aliquots were centrifuged and diluted 1:45 in PBS, resulting in a final protein concentration of about 2 mg/ml. Sulfo-NHS-biotin was then added to a final concentration of 10 mM and the samples were incubated on ice for 2 h. Unconjugated biotin was removed by dialysis against PBS at 4° C. for 72 h. Finally, the samples were aliquoted and stored at −20° C. prior to use.

Production and Purification of Recombinant Antibody Fragments

One hundred thirty five human recombinant scFv antibody fragments were selected against 65 antigens, mainly against immunoregulatory factors, using the n-CoDeR phage display library (25) (Table 4). The selection criteria were stringent, using standard operating procedures, to ensure the correct antibody specificity. All scFv probes were produced in 100 ml E. coli cultures, and purified from either expression supernatants or periplasmic preparations, using affinity chromatography on Ni-NTA agarose (Qiagen, Hilden, Germany). Elution was performed, using 250 mM immidazole, followed by extensive dialysis with PBS. The protein concentration was determined by measuring the absorbance at 280 nm, and the purified scFv was stored at 4° C. until further use.

Fabrication and Processing of Antibody Microarrays

The production and handling of the antibody microarrays was performed according to a previously optimized set-up (10, 25). Briefly, the scFv microarrays were fabricated, using a noncontact printer (Biochip Arrayer1, Perkin Elmer Life & Analytical Sciences, Wellesley, Mass., USA), which deposits approximately 330 pL/drop, using piezo technology. The scFv antibodies were arrayed by spotting 2 drops at each position, where the first drop was allowed to dry out before the second drop was dispensed. The solid support was the black polymer MaxiSorp microarray slides (NUNC A/S, Roskilde, Denmark) and each antibody was arrayed in eight replicates to ensure adequate statistics. To assist in the grid alignment during the subsequent quantification, a row containing Alexa647 conjugated streptavidin (2 µg/ml) was spotted as the top row in all eight subarrays that constituted the array. The slides were blocked with 5% (w/v) fat-free milk powder (Semper AB, Sundbyberg, Sweden) in PBS overnight and then placed in a Protein Array Workstation (PAW) (Perkin Elmer Life & Analytical Sciences) where they were washed for four minutes at 60 µl/min with 0.05% Tween-20 in PBS (PBS-T). Thereafter, 75 µl of the sample was injected and allow to agitated over the array every 15 seconds, for 60 minutes. After another four-minute wash, the arrays were incubated for 60 minutes with 350 µl of 1 µg/ml Alexa-647 conjugated streptavidin in PBS, with 1% (w/v) fat-free milk powder and 1% Tween 20. Finally, after a last washing step, the arrays were dried under a stream of nitrogen gas, and scanned with a confocal microarray scanner (ScanArray Express®, Perkin Elmer Life & Analytical Sciences) at 5 µm resolution, using three different scanner settings.

The ScanArray Express® software version 4.0 (Perkin Elmer Life & Analytical Sciences) was used to quantify the intensity of each spot, using the fixed circle method. The local background was subtracted, and to compensate for possible local defects, the two highest and lowest replicates were automatically excluded. In all further data analysis, each data point represents the mean value from the remaining four replicate spots. For protein analytes displaying saturated signals, values from lower scanner settings were used.

Microarray Data Normalization

Chip-to-chip normalization of the data set was performed, using a semi-global normalization approach, similar to the normalization method used for DNA microarrays. To find a scaling factor (7, 11, 27), the coefficient of variation (CV) was calculated for each antibody, and the 15% of antibodies displaying the lowest CV-values over all samples were identified, corresponding to 20 analytes. The normalization factor Ni was calculated by the formula $N_i=S_i/\mu$, where $S_i$ is the sum of the signal intensities of the 20 analytes for each sample, and µ is the average of $S_i$ from all samples. To normalize samples, all antibody intensities in a sample were divided with its normalization factor $N_i$.

Data Analysis

Classifier Calibration and Independent Testing

In order to reduce sample-to-sample variations, differences between t=0 and t=3-6 months protein expressions were used, as independent variables for an SVM classifier.

We trained and tested SVMs with a leave-one-out procedure, using N=38 samples and initially all M=135 variables. Since the number of antibodies exceeded the number of samples, we needed to eliminate those antibodies with low impact on the predictions in order to avoid fitting to noise due to random correlations. This was done for every leave-one-out sample using a backward elimination procedure. Performance was measured with the ROC (Receiver Operating Characteristics) area. The ranked antibody lists resulting from each SVM model were then fused into a consensus signature. The latter was then used with a frozen SVM on an independent test set. Below, the different steps are described in some detail and the full procedure is summarized in FIG. 5.

Leave-one-out Procedure

The principle for the procedure is to, for N samples belonging to two classes, train and test an SVM using leave-one out cross validation, i.e. to train the SVM on all but one samples, and to test the resulting model using the left out sample. The test sample is assigned a decision value using the trained SVM model, and is put back into the training set after which the next sample is left out to be used as a test sample. The procedure is repeated until each sample has been assigned a decision value once using all other samples as training set. The decision values for all samples are used to create a ROC curve, and the area under the curve is calculated. The obtained area serves as an estimation of the expected area for this sample set.

Backward Variable Elimination

In order to reduce the number of antibodies used for the classification we combined the above leave-one-out procedure with a backward elimination process for the antibodies.

This process will also produce a ranking of the antibodies with the purpose of assigning low ranks to randomly correlated antibodies.

The process is described in FIG. 5, to which references here are made as step 1-7.

Starting with M antibodies, M datasets are created where each dataset has one antibody replaced with a constant value, which is the average value of that antibody across all samples (step 1). To evaluate each antibody's importance for classification in the current dataset, a SVM leave-one-out procedure (as described above) is made for each of the M datasets. Subsequently, M ROC curves are created using the SVM output, and the dataset from which the ROC area generated had the smallest decrease (could be negative) compared to the original is identified. The antibody set to a constant value in that dataset is identified and eliminated (step 2). The datasets now contain M-1 antibodies and, M-1 new datasets are therefore created, all having one of the remaining antibodies replaced with the its average. The leave-one-out testing procedure together with the SVM evaluation using constant antibodies is repeated, eliminating, in effect, the next antibody carrying the least information. The procedure is continued until only one antibody remains, resulting in a rank order for each antibody's importance in the classification of the samples currently in the dataset (step 3). This information can then be used to build antibody sub-panels of any desired length (step 4). To evaluate the predicting power of such an antibody panel, it is not possible to test a new model using the same samples in an unbiased way. Furthermore, random correlated antibodies may still obtain a high rank. Therefore, an additional leave-one-out loop (step 5a) is added where one sample is removed before the initiation of the backward elimination procedure, which hence can be used as a test sample (step 5b). This outermost loop is iterated leaving each sample as a test set once, and the remaining samples to produce an antibody rank list. This rank list will then be used to pick a sub-panel of antibodies with the highest rank, and train a single SVM model, which is tested on the test sample. The result of the outermost leave-one-out process is a list of decision values for all samples, for any given sub-panel length. The corresponding ROC area serves as a test of the performance using antibody sub-panels of the given size, which can be used to estimate the number of antibody required to make an adequate classification in the dataset.

Consensus Antibody Signature

The backward elimination procedure results in the same number of antibody rank lists as the number of samples. To produce a single ranking order, the information from each run is concatenated into a consensus list by assigning each antibody a score (step 6) based on its average survival in the elimination rounds, where the antibody with the highest average survival is ranked as the most important. Finally, a new SVM was trained, using the 21 antibodies with the best scores, and tested on the new, independent, dataset (step 7).

Results

Serum Biomarker Signature Associated with Tumor Relapse

In an attempt to identify a serum biomarker signature that was predictive of distant recurrence in breast cancer, we collected samples from patients with primary breast cancer over a three year period. Finding a powerful classifier for metastatic disease by comparing the absolute serum protein (analyte) levels from the samples collected at the time of primary surgery was not successful, as was evident by a ROC area under the curve (AUC) of 0.54 (data not shown). Consequently, instead of comparing the absolute levels of the analytes, we analyzed the velocity which was defined as the log change for each analyte between the first serum sample drawn pre-operative and each consecutive sample from each patient over the three year period. Next, we fed the SVM the direction, i.e. up or down regulation and the magnitude of the change over time. The classifier allowed a stratification of patients into high vs. low risk for tumor recurrence with a ROC AUC of 0.88 (FIG. 1A), using serum samples collected 3-6 months after surgery. Hence, this approach based on biomarker velocity, demonstrated that there was enough information in the data set to identify a candidate biomarker signature that allowed a classification of patients and to identify a high-risk group for developing a distant tumor relapse within the three years.

Adopting the same strategy but instead using the samples collected at 12 months after surgery, we found a similar qualitative result but with a decreased prediction power, as illustrated by a ROC AUC of 0.75 (FIG. 1B). This trend could not be followed further, using samples collected at 24 and 36 months, since the patient cohort diagnosed with no metastatic disease was too small for a statistically relevant analysis.

Figure 2B:
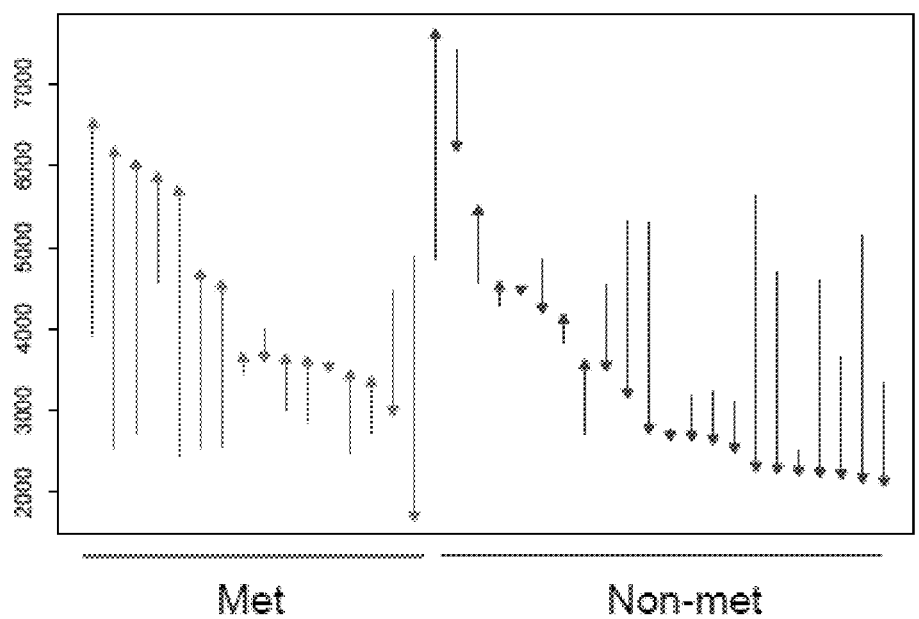
Figure 2C:
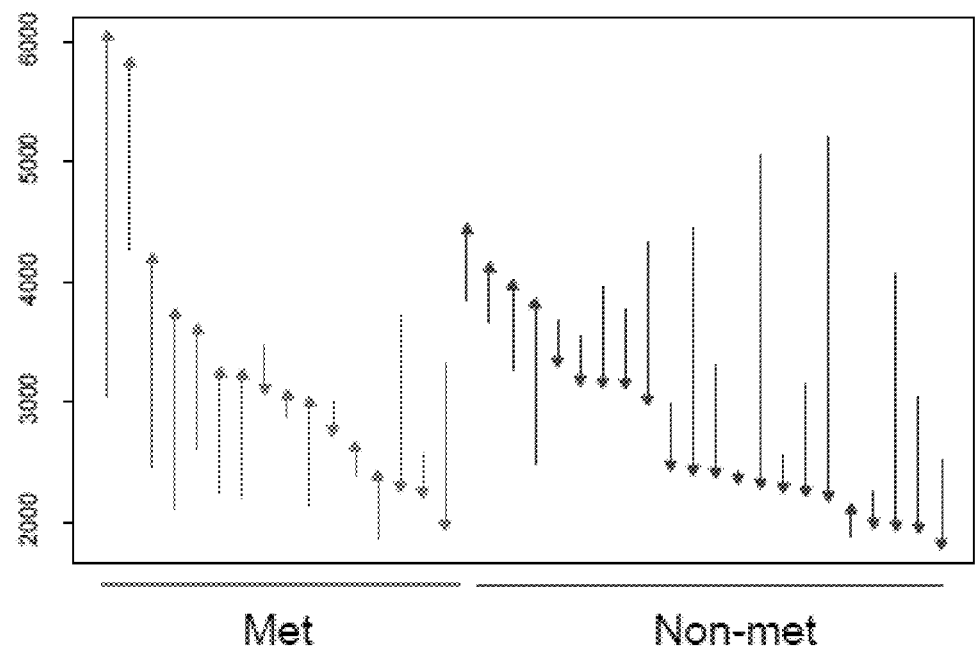
Figure 2D:
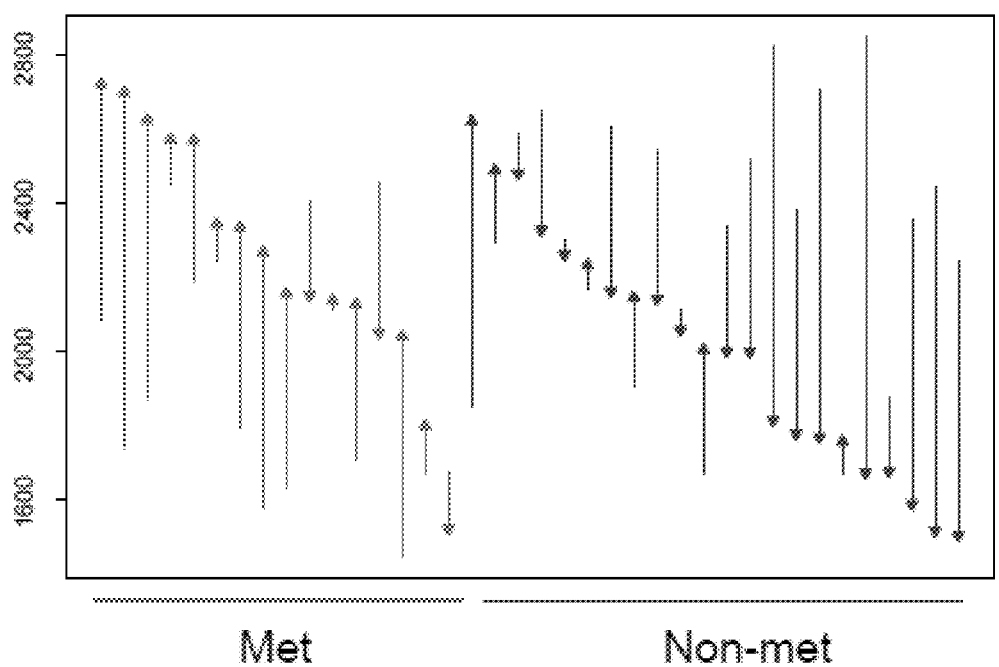

Analyzing all analytes (FIG. 2A), it was evident that increasing analyte velocities for metastatic patients during this period were clearly over-represented, while the opposite is true for non-metastatic patients. When the predictive biomarker signature was analyzed in more detail, Lewis x ($p=0.0005$), IL-16 ($p=0.002$) and CD40 ($p=0.0003$) were shown to differ the most between recurring vs. non-recurring breast cancer patients, during the first 6 months after surgery, as determined by Wilcoxon signed-rank test. In FIG. 2B-D, we show the dynamics for these three analytes, where it was evident that a significant increase during these first months after surgery was more frequent for patients developing a distant tumor relapse at a later time point.

Pre-validation of the Biomarker Signature Derived from the Discovery Cohort

To test the strength of the classification derived from the discovery cohort of 38 patients, we first condensed the total number of analytes down to the 21 non-redundant biomarkers contributing the most to the classification of metastatic relapse, using a backwards elimination strategy. The second independent patient cohort, denoted the pre-validation cohort, comprised of another 26 patients, of which 50% developed a distant breast cancer relapse within the three year period the studied lasted. Two serum samples were analyzed from each of the 26 new patients, the first collected at time of initial tumor resection and the second after 3 to 6 months, following the same procedure as for the discovery cohort. Consequently, 52 samples were processed with our antibody microarray platform, as described above, and the velocity of each biomarker was determined.

The classifier, consisting of the 21 most contributing biomarkers derived from the discovery cohort, allowed a stratification of patients into high vs. low risk for tumor recurrence with a ROC AUC of 0.85 in the independent, pre-validation cohort (FIG. 3). Of note, previously defined cancer associated biomarker signatures only overlapped to 30% with the present 21 biomarkers (7, 9, 11). Consequently, our predictive signature did not reflect a general inflammatory response (14).

The Effect of Adjuvant Chemotherapy on the Classification into High or Low Risk Groups To test if the classification, as displayed in FIG. 1, was dependent on the therapy received by the patients in the discovery cohort, we analyzed the effect of adjuvant chemotherapy on the classification into high or low risk of breast cancer recurrence. In FIG. 4, the SVM decision values for all patients and patient receiving chemotherapy, during the first 3-6 months, are indicated by arrows. No stratification of the individual chemotherapy receiving patients could be detected. Similar results were obtained when patients receiving adjuvant endocrine treatment were analyzed (data not shown). Hence, the classification into high and low risk groups for distant tumor relapse was not biased by a particular adjuvant therapy. Interestingly, since a few patients that received chemotherapy still after 6 months were classified as belonging to the high risk group, any beneficial effect of that particular therapy could not be demonstrated. Consequently, based on the molecular portrait derived from our microarray analysis these patients could be selected for another treatment regime.

Molecular Biomarker Signature Vs. Conventional Diagnostic Parameters

The power of molecular diagnostics has sometimes been questioned in particular in relation to the conventional clinical parameters (12), such as lymph node status, tumor size, histological grade, and oestrogen receptor (ER) and progesterone receptor (PgR) status. It is therefore essential to compare our serum predictor with the performance of predictors based upon such clinical markers. Utilizing the combination of conventional parameters, we compared them to our serum biomarker signature, which displayed a ROC AUC of 0.85 (FIG. 3A). Two additional SVM models were trained on the discovery dataset, using the clinical data and a combination of the clinical and microarray data, respectively.

The models were tested, using the patients in the pre-validation cohort, and the result was displayed as ROC curves. The ROC AUC for the predictor, using the conventional clinical parameters, was 0.66. Consequently, we achieved a significantly improved predictive power when using the molecular signature, based on analyte velocities. Of note, when we combined the conventional clinical parameters with our 21 biomarker signature and used both these as an approach for risk classification, we obtained a ROC AUC of 0.90 (FIG. 3B). Consequently, the two different sets of variables did not contain overlapping information with respect to the clinical outcome, as evident by a Pearson correlation analysis, which showed that the analyte velocities had very weak correlations (50.35) with the conventional clinical markers. This supports the fact that our protein serum approach contained unique information not present in conventional markers, which was in contrast to correlations observed between clinical markers and gene microarray profiling (12).

To further compare our data with available decision making tools, we investigated Adjuvant online (adjuvantonline.com), which estimates the risk for tumor relapse in breast cancer. The patient age, ER status, tumor grade, tumor size and the number of positive nodes were entered online and the calculated risk for relapse within ten years was recorded for each patient. The patients were then sorted according to their estimated risk and, using the true outcome for the patients in relation to distant recurrence, a ROC displaying an AUC of 0.60 was generated. This is in agreement with the AUC of 0.66 given by our analysis, based on conventional clinical parameters, although the disease-free follow up time was seven years in our pre-validation cohort.

Discussion

Breast cancer patients are treated with either local regional therapy or by the addition of systemic chemo, hormonal or biological therapies, resulting in improved clinical outcome, but also in a considerable over-treatment, with side effects for the patients and costs for health care providers. Prognostic parameters are consequently needed to stratify patients into different risk groups, which would aid in taking rational treatment decisions. Furthermore, predictive parameters for monitoring disease progression and therapy efficacy would be highly desirable, since it would allow patient based selection of adjuvant therapies and avoidance of over treatment. Today, patients with the same stage of disease can have completely different responses to therapy and overall survival, pointing to the fact that traditional parameters fail to accurately classify breast cancer patients, according to their clinical need.

Recent progress in gene expression profiling has, however, resulted in promising results for predicting the clinical outcome of breast cancer (5, 6), predict risk of developing local recurrence after breast-conserving surgery (14), as well as to earlier diagnosis of breast cancer (15). Since prediction of clinical outcome of breast cancer, based on gene expression profiles, requires presence of the tumor, gene based approaches do not allow for continuous disease monitoring and assessment of treatment efficacy after the initial tumor resection. For such purposes, the preferred choice of sample would be serum, which due to technical limitation has not been possible to analyze, using traditional proteomic approaches (16).

We have designed a recombinant antibody microarray platform (21-23), displaying high sensitivity and reproducibility and focused on serum proteins associated with the immune system. This affinity proteomics approach has recently already allowed the identification of several serum biomarker signatures distinguishing between different cancer indications and healthy individuals (7, 8, 11), demonstrating the power of the platform.

In an attempt to investigate if the information transiently stored in serum could be deciphered and aid in the management of breast cancer, we screened in total 64 patients with primary breast cancer and in total a few hundred serum samples for molecular portraits associated with the risk of develop distant tumor recurrence. Comparing samples collected over a three year period we could not decipher molecular patterns in the serum proteome, using static analyte levels, which indicated that the signals were either too weak, parallel instead of orthogonal variability vectors, or non-existing.

However, when analyzing the change in analyte intensity over time we could classify patients into a high and low risk group for developing metastatic breast cancer, within the period of the study. It was clear that during the first 3-6 months the discriminatory biomarkers increased in analytic intensity if a patient belonged to the high risk group and vice versa for the low risk patients. Most previous clinical proteomic studies are limited by the fact that only one cohort of patient is used to discover potential biomarker, and to circumvent this bottleneck we used a second, independent, cohort to test the ability to risk classify patients. For this purpose we first condensed the number of analytes used to pre-validate our candidate biomarker signature, using the unbiased backward elimination strategy. This resulted in the most discriminatory signature, which would not have been the case if only biomarkers with the lowest p-values were selected.

After condensation to 21 markers, we analyzed the test cohort and could classify the patients into high and low risk for developing metastatic breast cancer with a ROC AUC of 0.85. This decrease of predictive power was expected, since biomarkers always perform better in the data set from which they were derived. Still, a ROC AUC of 0.85 is the first demonstration that the information content harbored in a serum sample could be decoded, using an antibody microarray, which paves the way for developing a more personalized approach to the treatment of breast cancer patients. Of note, the signature did not seem to be affected by the therapy received by the patients, e.g. chemotherapy did not influence the stratification of patients. This observation (FIG. 4) also demonstrated the need for an accurate prediction of metastatic breast cancer, since several of the patients in the high-risk group might have benefitted from an other adjuvant treatment, just as some of the patients in the low risk group might have been over-treated.

To have a clinical impact, the serum based biomarkers have to outperform the traditional prognostic markers, such as clinical (age), histopathological (histological grade, lymph node status, tumor size) and hormone receptor status (ER, PgR) (14). Existing, pre-calibrated predictors based upon such markers cannot be used straightforwardly in this case, as they typically assume longer relapse times than the ones involved in our study and would be disfavored in a comparison. Therefore we assessed the predictive power of the traditional parameters by training and blind testing, using an SVM with these markers as input values. We demonstrated that even their combined power, represented by a ROC AUC 0.66, was significantly less than our pre-validated serum biomarker signature. This supports our hypothesis that there was enough information harbored in serum that could be deciphered, using a suitable technology, for disease prediction.

Interestingly, when we combined the traditional clinical parameters with our 21 biomarker signature, the predictive power increased resulting in an even more improved ROC AUC of 0.90, strongly suggesting that the serum markers provided added value. The present analysis was based upon 65 distinct analytes (Table 4) and, inspired by the present study, we will design an extended breast cancer chip able to analyze more serum proteins in larger patient cohorts, in order to further refine the biomarker signature and consequently increase its predictive power.

The biomarker signature that could classify patients into low or high risk for developing distant recurrence in breast cancer could, in a clinical setting, be used together with a biomarker signature associated with already diagnosed metastatic breast cancer (11). That signature (11) was based on eight biomarkers and has been shown to give a ROC AUC of 0.85 in an independent test cohort from the present study (data not shown). Consequently, a potential clinical application could be that after a risk assessment is performed on the patient at the first visit (3-6 months) after operation the signature associated with established metastatic breast cancer could be used to follow the patients over several years and monitor their molecular serum portraits to function as an early warning signal of tumor relapse. This has of course to be validated in larger prospective studies, but indicate a potential way forward towards a more personalized approach in breast cancer therapy.

In conclusion, we have demonstrated that a simple blood test harbor enough information to allow a risk assessment of the probability to develop metastatic breast cancer, after primary operation, using affinity proteomics.

REFERENCES

1. Parkin D M, Bray F, Ferlay J, Pisani P. Global cancer statistics, 2002. CA Cancer J Clin. 2005; 55:74-108.
2. Gonzalez-Angulo A M, Morales-Vasquez F, Hortobagyi G N. Overview of resistance to systemic therapy in patients with breast cancer. Adv Exp Med Biol. 2007; 608:1-22.
3. Eifel P, Axelson J A, Costa J et al. National Institutes of Health Consensus Development Conference Statement: adjuvant therapy for breast cancer, Nov. 1-3, 2000. J Natl Cancer Inst. 2001; 93:979-89.
4. Goldhirsch A, Ingle J N, Gelber R D. Et al Thresholds for therapies: highlights from the St Gallen international expert consensus on the primary therapy of early breast cancer 2009. Annals Oncol. 2009; 20:1319-1329.
5. van't Veer L J, Dai H, van de Vijver M J, et al. Gene expression profiling predicts clinical outcome of breast cancer. Nature 2002; 415:530-536.
6. Paik S, Shak S, Tang G et al. A multigene assay to predict recurrence of tamoxifen-treated, node-negative breast cancer. N. Engl. J. Med. 2004; 351:2817-2826.
7. Ingvarsson J, Wingren C, Carlsson A, et al. Detection of pancreatic cancer using antibody microarray-based serum protein profiling. Proteomics 2008; 8:2211-2219.
8. Sanchez-Carbayo M, Socci N D, Lozano J J, Haab B B, Cordon-Cardo C, Profiling bladder cancer using targeted antibody arrays. Am. J. Pathol. 2006; 168:93-103.
9. Ellmark P, Ingvarsson J, Carlsson A, et al. Identification of protein expression signatures associated with Helicobacter pylori infection and gastric adenocarcinoma using recombinant antibody microarrays. Mol. Cell. Proteomics 2006; 5:1638-1646.
10. Wingren C, Ingvarsson J, Dexlin L, Szul D and Borrebaeck C A K. Design of recombinant antibody microarrays for complex proteome analysis: Choice of sample labeling-tag and solid support. Proteomics 2007; 7:3055-3065.
11. Carlsson A, Wingren C, Ingvarsson J, et al. Serum proteome profiling of metastatic breast cancer using recombinant antibody microarrays. Eur. J. Cancer 2008; 44:472-480.
12. Edén P, Ritz C, Rose C, Fernö M, Peterson C. "Good Old" clinical markers have similar power in breast cancer prognosis as microarray gene expression profilers. Eur J Cancer. 2004; 40:1837-41.
13. Nimeus-Malmström E, Krogh M, Malmström P, et al. Gene expression profiling in primary breast cancer distinguishes patients developing local recurrence after breast-conservation surgery, with or without postoperative radiotherapy. Breast Cancer Res. 2008; 10:1-11.
14. Chelinska M, Kowalewska M. Systemic inflammation as a confounding factor in cancer biomarker discovery and validation. Nature 2010; 10; 2.

15. Sharma P, Sahni N S, Tibshirani R, et al. Early detection of breast cancer based on gene-expression patterns in peripheral blood. Breast Cancer Res. 2005; 7:634-44.
16. Aebersold R, Mann M. Mass spectrometry-based proteomics. Nature 2003; 13:198-207.
17. Ekins R P. Ligand assays: from electrophoresis to miniaturized microarrays. Clin. Chem. 1998; 44:2015-2030.
18. Zhu H, Snyder M. Protein chip technology. Curr Opin Chem Biol 2003; 7:55-63.
19. Anderson N L, Anderson N G. The human plasma proteome: history, character, and diagnostic prospects. Mol. Cell. Proteomics 2002; 1:845-867.
20. Borrebaeck C A K, Wingren C. Design of high-density antibody microarrays for disease proteomics: Key technological issues. J Proteomics 2009; 72:928-935.
21. Steinhauer C, Wingren C, Malmborg Hager A C and Borrebaeck C A K. Single framework recombinant antibody fragments designed for protein chip applications. Biotechniques 2002; Suppl.: High-Throughput Proteomics: Protein Arrays:38-45
22. Wingren C, Steinhauer C, Ingvarsson J, et al. Microarrays based on affinity-tagged scFv antibodies: sensitive detection of analyte in complex proteomes. Proteomics 2005; 5:1281-1291
23. Borrebaeck C A K and Wingren C. High-throughput proteomics using antibody microarrays: an update. *Expert Rev Mol Diagn.* 2007; 7:673-686.
24. Söderlind E, Strandberg L, Jirholt P, et al. Recombining germline-derived CDR sequences for creating diverse single-framework antibody libraries. Nat Biotechnol 2000; 18:852-856
25. Ingvarsson J, Larsson A, Sjoholm A G, et al. Design of recombinant antibody microarrays for serum protein profiling: targeting of complement proteins. J. Proteome Res. 2007; 6:3527-36.
26. Hamelinck D, Zhou H, Li L, et al. Optimized normalization for antibody microarrays and application to serum-protein profiling. Mol Cell Proteomics 2005; 4:773-84.

TABLE 1

| Biomarker name | Exemplary sequence(s) |
|---|---|
| (A) Core biomarkers | |
| Apolipoprotein A4 (APOA4) | P06727 |
| ATP synthase subunit beta, mitochondrial (ATP5B) | P06576 |

TABLE 1-continued

| Biomarker name | Exemplary sequence(s) |
|---|---|
| (B) Preferred biomarker signature | |
| Bruton's tyrosine kinase (BTK) | Q06187 |
| Complement-1 esterase inhibitor (C1 esterase inhibitor) | P05155 |
| Complement factor B (Factor B) | P00751 |
| CD40 | Q6P2H9 |
| Homeodomain transcription factor CHX10 (CHX10) | P05155 |
| Interleukin-1α (IL-1α) | P01583 |
| Interleukin-5 (IL-5) | BC066282, CH471062, P05113 |
| Interleukin-6 (IL-6) | P05231 |
| Interleukin-7 (IL-7) | AK226000, AB102893, AB102885, P13232 |
| Interleukin-9 (IL-9) | P15248 |
| Interleukin-12 (IL-12) | O60595 |
| Interleukin-13 (IL-13) | P35225 |
| Interleukin-18 (IL-18) | Q14116 |
| TBC1 domain family member 9 (KIAA0882) | Q6ZT07 |
| Lewis$^x$/CD15 | [Not applicable] |
| Oxysterol binding protein-like 3 (OSBPL3) | C9JEF2, C9JZ19, Q9H4L5, C9J8P4 |
| Monocyte chemotactic protein-1 (MCP-1) | P13500 |
| Sialyl Lewis$^x$ | Carbohydrate structure [Not applicable] |
| Tumour necrosis factor-1 β (TNF-β) | P01374 |
| (C) Optional additional biomarkers | |
| Integrin alpha-10 | Hs. 158237 |
| β-galactosidase | P16278 |
| CD40 ligand | P29965 |
| Eotaxin | P51671 |
| Glucagon-like peptide-1 receptor (GLP-1 R) | P43220 |
| Interleukin-1β | P01584 |
| Interleukin-3 | P08700 |
| Interleukin-8 | CR623827, CR623683, DQ893727, DQ890564, P10145 |
| Interleukin-10 | P22301 |
| Interleukin-16 | Q05BE6, Q8IUU6, B5TY35 |
| MCP-4 | Q99616 |
| Myomesin-2 (MYOM2) | P54296 |
| Rantes | P13501 |
| Transforming growth factor-β (TGF-β1) | P01137 |
| Regulator of nonsense transcripts 3B (UPF3B) | Q0VAK7 |
| Interleukin-4 | P05112 |
| Interleukin-1ra | P18510 |

TABLE 2

The following parameters were obtained using the e1071 1.5-24 SVM, available from http://cran.r-project.org/web/packages/e1071/index.html.

$type

[1] 0

$kernel

[1] 0

$cost

[1] 1

$degree

[1] 3

$gamma

[1] 0.04761905

TABLE 2-continued

The following parameters were obtained using the e1071 1.5-24 SVM, available from http://cran.r-project.org/web/packages/e1071/index.html.

$coef0

[1] 0
$nu

[1] 0.5
$epsilon

[1] 0.1
$sparse

[1] FALSE
$scaled

[1] TRUE TRUE TRUE TRUE TRUE TRUE TRUE TRUE TRUE TRUE TRUE TRUE TRUE TRUE TRUE TRUE TRUE TRUE TRUE
$x.scale
$x.scale$'scaled:center'

| IL.7..1. | TNF.b..2. | EG7.141932.CHX10 | BTK | CD40..4. | EG22.260123.APOA4 |
|---|---|---|---|---|---|
| 0.6093909 | 0.4888461 | 0.5194064 | 0.3885171 | 0.4091274 | 0.5693457 |
| EG23.252478.KIAA0882 | EG25.252336.anti.MCL | EG9.350100.ATP5B | EI | Factor.B..2.. | IL.12..3. |
| 0.4535247 | 0.5956616 | 0.5668468 | 0.5194224 | 0.5307535 | 0.4051029 |
| IL.13..3. | IL.18..1. | IL.1a..3. | IL.5..2. | IL.6..1. | IL.9..2. |
| 0.5284938 | 0.4075885 | 0.5941146 | 0.5428361 | 0.3743462 | 0.5567893 |
| Lewisx..1. | MCP.1..3. | Sialle.x | | | |
| 0.5204801 | 0.5608207 | 0.5048063 | | | |

$x.scale$'scaled:scale'

| IL.7..1. | TNF.b..2. | EG7.141932.CHX10 | BTK | CD40..4. | EG22.260123.APOA4 |
|---|---|---|---|---|---|
| 0.2234510 | 0.2340201 | 0.2253392 | 0.1617694 | 0.2003829 | 0.1947099 |
| EG23.252478.KIAA0882 | EG25.252336.anti.MCL | EG9.350100.ATP5B | EI | Factor.B..2.. | IL.12..3. |
| 0.1673467 | 0.2073111 | 0.2686860 | 0.2275948 | 0.2338916 | 0.1468782 |
| IL.13..3. | IL.18..1. | IL.1a..3. | IL.5..2. | IL.6..1. | IL.9..2. |
| 0.2020372 | 0.1715512 | 0.2541235 | 0.2015772 | 0.2359194 | 0.2176524 |
| Lewisx..1. | MCP.1..3. | Sialle.x | | | |
| 0.2520771 | 0.2209286 | 0.2607917 | | | |

$y.scale

NULL
$nclasses

[1] 2
$levels

[1] "DistantMet"   "NoDistantMet" "rest"
$tot.nSV

[1] 16
$nSV

[1] 5 11
$labels

[1] 1 2
$SV

| | IL.7..1. | TNF.b..2. | EG7.141932.CHX10 | BTK | CD40..4. | EG22.260123.APOA4 |
|---|---|---|---|---|---|---|
| BC104 | −1.72878005 | 0.16404151 | 0.08194673 | −1.4821892 | −0.20945935 | −0.008551152 |
| BC152 | −1.18673489 | 0.16789721 | −0.37353361 | −0.2558364 | −0.07045099 | −0.300217895 |
| BC156 | 1.07470984 | −1.25840379 | 0.14648518 | 0.5124307 | 0.43604106 | 0.701639774 |
| BC224 | −0.38641301 | −0.38465450 | 0.58904238 | −0.2198718 | 0.18262343 | 0.971031555 |
| BC70 | 0.49494080 | 0.02968846 | −0.02015569 | 1.4284150 | 0.55805233 | 1.001445091 |
| BC119 | 0.68089956 | −0.26970554 | 0.01709544 | 1.2594195 | 0.80095567 | 0.985860689 |
| BC123 | −1.47972460 | −0.64487597 | 0.23352593 | −2.4016723 | −0.30192272 | −0.613369998 |
| BC162 | 0.08652534 | −0.49958930 | −0.62779888 | 0.4662603 | −1.62702240 | −1.265192129 |
| BC212 | −0.25019319 | 0.62731854 | −0.15142958 | −1.3452997 | −2.04172864 | −0.862262747 |
| BC41 | −0.56280296 | −0.20014615 | 0.81993713 | −0.2446241 | 0.40022261 | 1.011699296 |
| BC44 | 0.34946805 | −0.35003605 | −0.28882815 | −0.2513542 | 0.43765530 | −0.729949938 |
| BC57 | 1.07732967 | 1.42323505 | 2.12950113 | −0.4789719 | 0.67120469 | 1.438276723 |
| BC82 | −0.85194455 | −0.02634785 | −0.07671850 | −1.0847651 | 0.29761712 | −0.037555372 |
| BC87 | −0.09104134 | 0.55117224 | −0.21032290 | 0.3012652 | 0.24433613 | −0.386117835 |
| BC92 | 0.61584785 | 1.38011151 | 0.70604393 | 0.1980872 | 0.37732185 | 0.401803985 |
| BC98 | −0.09870669 | −2.08890693 | 0.53803970 | −0.2163412 | −0.79686632 | 0.438660744 |
| | EG23.252478.KIAA0882 | EG25.252336.anti.MCL | EG9.350100.ATP5B | EI | Factor.B..2.. | IL.12..3. | IL.13..3. |
| BC104 | 0.56474259 | 0.647552034 | −0.06841983 | −0.79806974 | −0.4818731 | −0.4980696 | −1.00268354 |
| BC152 | −0.13423148 | −0.255316821 | −0.81984741 | −0.46271285 | 0.4618282 | −0.3297756 | −0.27851745 |
| BC156 | 0.30184949 | 0.112261016 | 1.20529203 | 0.67424741 | −0.8271355 | 0.6113120 | 0.25845095 |
| BC224 | 0.51977281 | 0.556924433 | 1.61211669 | 0.06826851 | 0.1333717 | −0.4364411 | −0.02215751 |
| BC70 | −0.17663963 | 0.309008339 | 0.52641522 | 1.03788753 | 1.6460879 | 0.8074381 | 0.58898984 |
| BC119 | 0.32059607 | 0.962229843 | 0.60826765 | 0.62258224 | −2.1781676 | 0.8169730 | 2.33375910 |

TABLE 2-continued

The following parameters were obtained using the e1071 1.5-24 SVM, available from http://cran.r-project.org/web/packages/e1071/index.html.

| | | | | | | | |
|---|---|---|---|---|---|---|---|
| BC123 | 1.31842626 | 0.791827496 | −0.24189341 | −2.28222440 | 1.2468878 | −2.7580871 | −1.54337127 |
| BC162 | −0.63413299 | −1.026124999 | −1.61374915 | −0.73716455 | −0.1773728 | 0.4033345 | −0.86244597 |
| BC212 | 0.12307725 | −0.006164769 | −0.02665158 | −1.43219060 | 0.1276030 | −0.3183847 | −0.48332555 |
| BC41 | 1.81890868 | 0.941110371 | 0.68983913 | 1.46753304 | 0.3906515 | −0.3938307 | −0.44744993 |
| BC44 | −0.31092196 | −0.205794722 | −0.85059772 | −0.41608430 | −0.9024877 | −0.3314940 | −0.02539801 |
| BC57 | 3.26552710 | 1.931485894 | 0.94863487 | −1.55045128 | −0.7237189 | −0.2999112 | −1.32472302 |
| BC82 | 0.35122821 | −0.190928380 | 0.44597738 | −0.23940059 | 0.2982282 | −0.7716297 | 0.09473559 |
| BC87 | −0.71641769 | −0.673912564 | −0.43323779 | 0.94550916 | 0.8373675 | 1.0839010 | −0.30577379 |
| BC92 | 0.01251850 | 0.340860075 | 0.69062228 | −1.09554932 | 0.1361003 | −0.3563486 | 0.08877688 |
| BC98 | 0.50131918 | −0.334405791 | 0.86837302 | −0.21731264 | 0.2780535 | −1.1415435 | 2.18218964 |
| | IL..18..1. | IL.1a..3. | IL..5..2. | IL..6..1. | IL..9..2. | Lewisx..1. | MCP.1..3. | Sialle.x |
| BC104 | −0.24927827 | −0.3977183 | −0.84185368 | −0.03695358 | −0.884569546 | 0.04913151 | −1.1699038164 | 0.48580074 |
| BC152 | 0.11636339 | 0.4584601 | −0.95665226 | −1.58675456 | −0.859445462 | 0.19352752 | −0.7047500356 | 0.40039174 |
| BC156 | −0.04614928 | −0.1349133 | 0.48169777 | −1.36041255 | 0.394145570 | −0.72699766 | 0.1762927414 | −0.78994670 |
| BC224 | −2.37589954 | 0.3223370 | −0.06663768 | −1.35422913 | −1.295940601 | −2.06476589 | 1.1772446443 | −0.17406871 |
| BC70 | 0.39387896 | 1.1476412 | 0.30869312 | 0.60644973 | 0.881224796 | 0.45931367 | 1.7611954453 | −1.03576811 |
| BC119 | 0.27336511 | 1.0704331 | 0.21547230 | −1.07250229 | 2.004479796 | −1.73469677 | 1.4619597768 | 1.21056825 |
| BC123 | −0.71185770 | −1.1497185 | −1.75367819 | −1.10930970 | −2.558158402 | −0.92230494 | −1.8412777307 | 1.58508822 |
| BC162 | −0.55776651 | −0.9937919 | −0.96602749 | 0.69835443 | −0.250338305 | 0.07699985 | 0.0406312609 | 1.57473207 |
| BC212 | −0.04380831 | −2.1500522 | −0.43269681 | 0.03655087 | −1.532758825 | 0.19392949 | −0.3019735097 | 0.81326702 |
| BC41 | 3.45326238 | 0.2856195 | 0.77145772 | 0.60966231 | −0.262739745 | −0.19053962 | 0.2703781740 | −0.06397621 |
| BC44 | −0.48721493 | 0.4488824 | 1.27502167 | 0.63585407 | 0.510734350 | 1.01036207 | −0.7046768943 | 0.51387072 |
| BC57 | −0.15814942 | −0.7699348 | −1.08134602 | 0.41453433 | 0.007046511 | −0.32801357 | 0.6285212119 | −0.28667503 |
| BC82 | 0.31271803 | 0.8128847 | −0.40799788 | −0.48090892 | −0.275352403 | −0.25212082 | −0.3259224211 | −0.18688331 |
| BC87 | −0.39521361 | 0.7705388 | −0.26220576 | −0.96962268 | 0.729620447 | −0.32483706 | 0.8884765739 | −1.77813625 |
| BC92 | −0.08982865 | −0.1900476 | −0.31901322 | 0.64425431 | −0.230280344 | −0.10882989 | 0.0009727735 | −0.49132772 |
| BC98 | −0.11678834 | −0.0551481 | 0.07821912 | −1.12818573 | 0.156899742 | −1.38143674 | −0.3223663269 | 0.66550080 |

$index

[1] 1 5 6 15 16 19 20 23 25 27 28 30 35 36 37 38
$rho

[1] 0.2847347
$compprob

[1] TRUE
$probA

[1] −1.094657
$probB

[1] 0.2128045
$sigma

[1] 0
$coefs    [,1]

| | |
|---|---|
| [1,] | 0.79306050 |
| [2,] | 0.81101350 |
| [3,] | 0.50522912 |
| [4,] | 0.08584558 |
| [5,] | 0.62204473 |
| [6,] | −0.28084545 |
| [7,] | −0.43343460 |
| [8,] | −0.08939337 |
| [9,] | −0.04883494 |
| [10,] | −0.28094053 |
| [11,] | −0.19803954 |
| [12,] | −0.01242534 |
| [13,] | −0.40895362 |
| [14,] | −0.87795820 |
| [15,] | −0.14985990 |
| [16,] | −0.03650794 |

$na.action

NULL
$fitted

| | | | | | | | | |
|---|---|---|---|---|---|---|---|---|
| BC104 | BC140 | BC146 | BC149 | BC152 | BC156 | BC163 | BC171 | BC178 |
| DistantMet | DistantMet | DistantMet | DistantMet | DistantMet | DistantMet | DistantMet | DistantMet | DistantMet |
| BC181 | BC193 | BC198 | BC208 | BC221 | BC224 | BC70 | BC108 | BC115 |
| DistantMet | DistantMet | DistantMet | DistantMet | DistantMet | DistantMet | DistantMet | NoDistantMet | NoDistantMet |
| BC119 | BC123 | BC128 | BC135 | BC162 | BC185 | BC212 | BC217 | BC41 |
| NoDistantMet | NoDistantMet | NoDistantMet | NoDistantMet | NoDistantMet | NoDistantMet | NoDistantMet | NoDistantMet | NoDistantMet |
| BC44 | BC48 | BC57 | BC62 | BC66 | BC74 | BC78 | BC82 | BC87 |

TABLE 2-continued

The following parameters were obtained using the e1071 1.5-24 SVM, available from http://cran.r-project.org/web/packages/e1071/index.html.

| | | | | | | | | |
|---|---|---|---|---|---|---|---|---|
| NoDistantMet BC92 | NoDistantMet BC98 | NoDistantMet | NoDistantMet | NoDistantMet | NoDistantMet | NoDistantMet | NoDistantMet | NoDistantMet |
| NoDistantMet | NoDistantMet | | | | | | | |

Levels:
DistantMet
NoDistantMet
rest

TABLE 3

Patient demographics and clinical parameters

| | Discovery cohort | | Pre-validation cohort | |
|---|---|---|---|---|
| Group | Met | Non Met | Met | Non Met |
| Number of patients | 16 | 22 | 13 | 13 |
| Disease-free follow-up (3/5/7 years)[a] | — | 4/14/4 | — | —/12/1 |
| Age | 54 (14)[b] | 52 (12) | 59 (13) | 60 (9) |
| Sample 2, collection time after OP (months) | 4.4 (1.1) | 4.5 (1.1) | 4.9 (2.1) | 4.0 (1.0) |
| Sample 3, collection time after OP (months) | 13 (1.0) | 13 (1.2) | — | — |
| Time to relapse (months) | 21 (10) | — | 19 (13) | — |
| Tumor size (mm) | 22 (10) | 21 (11) | 38 (23) | 16 (11) |
| Pre/Post menopausal | 5/11 | 10/12 | 9/4 | 11/2 |
| ER+/− | 13/2[c] | 18/4 | 9/4 | 11/1 |
| PgR+/− | 9/6 | 13/9 | 7/6 | 7/5 |
| Lymph node+/− | 12/4 | 10/11 | 6/5 | 3/9 |
| Grade I/II/III | 1/9/5 | 3/13/5 | 0/9/4 | 5/6/1 |
| Ductal/Lobular | 16/1[d] | 20/2 | 11/2 | 11/2 |
| Radiation/No Radiation | 11/5 | 14/8 | 11/2 | 9/4 |
| Adjuvant therapy: Hormonal (tamoxifen) | 12/4 | 16/6 | 6/7 | 7/6 |
| Adjuvant therapy: Aromatase inhibitor | 6/10 | 3/19 | 4/9 | 4/9 |

[a]Time of disease-free follow-up, for non-metastatic patients.
[b]Values in parenthesis are standard deviations.
[c]In cases where the sum is less than the number in the group, patient data is missing.
[d]In the case of Ductal/Lobular tumor type, patients may have both, resulting in a sum larger than the number of patients in the group.

TABLE 4

Summary of biomarkers analysed by the microarray
Antigen (no. of clones)

Alfa-10 (1)
Alfa-11 (1)
Angiomotin (2)
APOA4 (3)*
ATP5B (3)*
β-galactosidase (1)
BTK (1)*
C1q (1)**
C1s (1)
C1 esterase inhibitor (1)*
C3 (2)**
C4 (1)
C5 (2)
CD40 (4)*
CD40 ligand (1)
CHX10 (3)*
Digoxin (1)
DUSP9 (1)
Eotaxin (3)
Factor B (2)*/**
GLP-1 (1)
GLP-1 R (1)
GM-CSF (3)
IL-1α (3)*
IL-1β (3)
IL-1ra (3)

TABLE 4-continued

Summary of biomarkers analysed by the microarray
Antigen (no. of clones)

IL-2 (3)
IL-3 (3)
IL-4 (3)**
IL-5 (3)*/**
IL-6 (4)*/**
IL-7 (2)*
IL-8 (3)
IL-9 (3)*
IL-10 (3)**
IL-11 (3)
IL-12 (4)*
IL-13 (2)*/**
IL-16 (2)
IL-18 (3)*
INF-γ (2)
JAK3 (1)
KIAA0882 (3)*
LDL (2)
Leptin (1)
Lewis$^x$ (2)*
Lewis$^y$ (1)
LUM (1)
OSBPL3 (2)*
MCP-1 (3)*/**
MCP-3 (1)
MCP-4 (2)
MYOM2 (2)
Procathepsin (1)
Properdin (1)
PSA (1)
Rantes (1)
Sialyl lewis$^x$ (1)*
TGF-β1 (2)
TM peptide (1)
TNF-α (2)
TNF-β (4)*
UPF3B (3)
VEGF (4)

*Included in the 21 biomarker signature
**Antibody specificity against these antigens were further validated, by mass spectrometry, protein arrays, or ELISA.

The invention claimed is:

1. A method for the prognosis and treatment of breast cancer in a human subject with primary breast cancer comprising the steps of:
    (a) providing a first proteome sample from the subject, wherein the proteome sample is a serum or plasma sample;
    (b) measuring in the first proteome sample the amount of two or more biomarkers selected from the group of biomarkers in Table 1, wherein the two or more biomarkers comprise Apolipoprotein A4 (APOA4) and ATP synthase subunit beta, mitochondrial (ATP5B);
    (c) providing an additional proteome sample from the subject, wherein the proteome sample is a serum or plasma sample;
    (d) measuring in the additional proteome sample the amount of the two or more biomarkers measured in step (b);

(e) determining the difference between the amount of the two or more biomarkers in the first proteome sample and the additional proteome sample;

(f) calculating a biomarker velocity for each of the two or more biomarkers;

(g) determining a risk of recurrence of breast cancer in the subject based on the biomarker velocity for each of the two or more biomarkers, using a support vector machine trained with a dataset for the two or more biomarkers; and (h) treating the subject with a therapy selected on the basis of the level of risk of recurrence of breast cancer in the subject, wherein the therapy is selected from the group consisting of local regional therapy, systemic chemotherapy, systemic hormonal therapy and systemic biological therapy, wherein step (b) and step (d) are performed using an array comprising antibodies or antigen-binding fragments thereof that bind to each of the two or more biomarkers and the resultant biomarker data are normalized prior to step (e).

2. The method according to claim 1 wherein steps (c) and (d) are repeated in order to provide one or more further proteome samples from the subject and to measure therein the amount of the one or more biomarkers measured in step (b), wherein the one or more further proteome samples are representative of the proteome composition of the subject on different days from the first and second proteome samples.

3. The method according to claim 1 wherein step (b) further comprises measuring the amount of 1 or more biomarkers from the biomarkers listed in Table 1(B).

4. The method according to claim 1 wherein step (b) further comprises measuring the amount of 1 or more biomarkers from the biomarkers listed in Table 1(C).

5. The method according to claim 1 wherein step (b) comprises measuring the amount of all of the biomarkers listed in Table 1.

6. The method according to claim 1 wherein the samples provided in step (a) and/or step (c) are treated prior to step (b) and/or step (d), respectively, such that any biomarkers present in the samples are labelled with a detectable moiety.

7. The method according to claim 1 wherein the first proteome sample and additional proteome sample are representative of the proteome composition of the subject on different days at least 7 days apart.

8. The method according to claim 1 wherein the first proteome sample, provided in step (a), is representative of the proteome composition of the subject at a time point within about 4 weeks before or after resection of a breast cancer tumour in the subject.

9. The method according to claim 1 wherein the first proteome sample is representative of the proteome composition of the subject at a time point about 4 weeks before resection of a breast cancer tumour in the subject.

10. The method according to claim 1 wherein the additional proteome sample is representative of the proteome composition of the subject at a time point within 3 to 6 months after tumour resection.

11. The method according to claim 1 wherein step (c) and step (d) are repeated such that further proteome samples are provided and biomarker levels therein measured, wherein the further proteome samples are representative of the proteome composition of the subject at a time point every 6 to 18 months after tumour resection, up to at least 24 months.

12. The method according to claim 1 wherein the predicative accuracy of the method, as determined by an ROC AUC value, is at least 0.70.

13. An array for performing the method according to claim 1 comprising two or more binding agents each capable of binding to a biomarker listed in Table 1, wherein the two or more binding agents comprise binding agents which bind Apolipoprotein A4 (APOA4) and ATP synthase subunit beta, mitochondrial (ATP5B), and wherein said binding agents are antibodies or antigen-binding fragments thereof.

14. The array according to claim 13 comprising one or more binding agents capable of binding to each of the biomarkers listed in Table 1.

15. A kit for performing a method according to claim 1 comprising two or more binding agents each capable of binding to a biomarker listed in Table 1, wherein the two or more binding agents comprise binding agents which bind Apolipoprotein A4 (APOA4) and ATP synthase subunit beta, mitochondrial (ATP5B), and wherein said binding agents are antibodies or antigen-binding fragments thereof.

16. The method according to claim 1, wherein the first proteome sample is collected within 4 weeks before or after tumour resection of the subject and wherein the additional proteome sample is collected within 3 to 9 months of tumour resection of the subject.

17. The method according to claim 1, wherein the therapy comprises treating the subject with tamoxifen.

18. The method according to claim 16, wherein the therapy comprises treating the subject with tamoxifen.

* * * * *